(12) United States Patent
Godek et al.

(10) Patent No.: US 12,137,899 B2
(45) Date of Patent: Nov. 12, 2024

(54) MULTIPLE SUTURE PLACEMENT SYSTEM

(71) Applicant: Cypris Medical, Inc., Chicago, IL (US)

(72) Inventors: Christopher P. Godek, Sea Girt, NJ (US); Michael V. Chobotov, Carlsbad, CA (US); Daniel Holton, Evanston, IL (US)

(73) Assignee: Cypris Medical, Inc., Chicago, IL (US)

( * ) Notice: Subject to any disclaimer, the term of this patent is extended or adjusted under 35 U.S.C. 154(b) by 8 days.

(21) Appl. No.: 17/315,119

(22) Filed: May 7, 2021

(65) Prior Publication Data
US 2021/0346010 A1   Nov. 11, 2021

Related U.S. Application Data

(60) Provisional application No. 63/022,632, filed on May 11, 2020.

(51) Int. Cl.
*A61B 17/04*   (2006.01)

(52) U.S. Cl.
CPC ...... *A61B 17/0483* (2013.01); *A61B 17/0482* (2013.01)

(58) Field of Classification Search
CPC ............ A61B 17/0469; A61B 17/0482; A61B 17/0483; A61B 2017/00792; A61B 2017/0472; A61B 2017/0495; A61B 17/062
See application file for complete search history.

(56) References Cited

U.S. PATENT DOCUMENTS

| | | |
|---|---|---|
| 3,206,217 A | 9/1965 | Shepard et al. |
| 4,210,148 A | 7/1980 | Stivala |
| 4,268,481 A | 5/1981 | Souvaniemi et al. |
| 4,373,530 A | 2/1983 | Kilejian |
| 4,841,888 A | 6/1989 | Mills et al. |
| 4,950,283 A | 8/1990 | Dzubow et al. |
| 5,080,663 A | 1/1992 | Mills et al. |
| 5,312,422 A | 5/1994 | Trott |
| 5,507,754 A | 4/1996 | Green et al. |
| 5,525,302 A | 6/1996 | Astle |
| 5,549,617 A | 8/1996 | Green et al. |
| 5,562,686 A | 10/1996 | Sauer et al. |
| 5,766,186 A | 6/1998 | Faraz et al. |
| 5,792,153 A | 8/1998 | Swain et al. |
| 5,792,163 A | 8/1998 | Swain et al. |

(Continued)

FOREIGN PATENT DOCUMENTS

| | | |
|---|---|---|
| CN | 206777365 | 12/2017 |
| EP | 0674875 A1 | 10/1995 |

(Continued)

OTHER PUBLICATIONS

PCT International Patent Application No. PCT/US21/31564, International Search Report and Written Opinion of the International Searching Authority mailed Oct. 27, 2021, 19 pages.

(Continued)

*Primary Examiner* — Darwin P Erezo
*Assistant Examiner* — Christian D Knauss
(74) *Attorney, Agent, or Firm* — Craig R. Miles; CR MILES P.C.

(57) ABSTRACT

A suturing system including apparatus and methods for disposing sutures in a substrate.

2 Claims, 27 Drawing Sheets

(56) References Cited

U.S. PATENT DOCUMENTS

| | | | |
|---|---|---|---|
| 5,797,927 A | 8/1998 | Yoon | |
| 5,908,426 A | 6/1999 | Pierce | |
| 5,954,057 A | 9/1999 | Li | |
| 5,984,932 A | 11/1999 | Yoon | |
| 6,048,351 A | 4/2000 | Gordon et al. | |
| 6,059,800 A | 5/2000 | Hart et al. | |
| 6,077,276 A | 6/2000 | Kontos | |
| 6,155,989 A | 12/2000 | Collins | |
| 6,346,111 B1 | 2/2002 | Gordon et al. | |
| 6,428,549 B1 | 8/2002 | Kontos | |
| 6,464,707 B1 | 10/2002 | Bjerken | |
| 6,533,796 B1 | 3/2003 | Sauer et al. | |
| 6,936,054 B2 | 8/2005 | Chu | |
| 6,955,643 B2 | 10/2005 | Gellman et al. | |
| 6,997,931 B2 | 2/2006 | Sauer et al. | |
| 7,033,370 B2 | 4/2006 | Gordon et al. | |
| 7,060,077 B2 | 6/2006 | Gordon et al. | |
| 7,060,079 B2 | 6/2006 | Wulc et al. | |
| 7,063,710 B2 | 6/2006 | Takamoto et al. | |
| 7,175,636 B2 | 2/2007 | Yamamoto et al. | |
| 7,220,266 B2 | 5/2007 | Gambale | |
| 7,399,304 B2 | 7/2008 | Gambale et al. | |
| 7,442,198 B2 | 10/2008 | Gellman et al. | |
| 7,517,356 B2 | 4/2009 | Heinrich | |
| 7,731,727 B2 | 1/2010 | Sauer | |
| 7,763,036 B2 | 7/2010 | Stokes et al. | |
| 7,780,684 B2 | 8/2010 | Wulc et al. | |
| 7,833,236 B2 | 11/2010 | Stokes et al. | |
| 7,846,169 B2 | 12/2010 | Shelton, IV et al. | |
| 7,951,157 B2 | 5/2011 | Gambale | |
| 8,057,386 B2 | 11/2011 | Azonian et al. | |
| 8,075,573 B2 | 12/2011 | Gambale et al. | |
| 8,100,920 B2 | 1/2012 | Gambale et al. | |
| 8,177,794 B2 | 5/2012 | Cabrera et al. | |
| 8,177,797 B2 | 5/2012 | Shimoji et al. | |
| 8,206,284 B2 | 6/2012 | Azonian et al. | |
| 8,226,665 B2 | 7/2012 | Cohen | |
| 8,246,637 B2 | 8/2012 | Viola et al. | |
| 8,257,369 B2 | 9/2012 | Gellman et al. | |
| 8,286,847 B2 | 10/2012 | Taylor | |
| 8,292,886 B2 | 10/2012 | Kerr et al. | |
| 8,292,905 B2 | 10/2012 | Taylor et al. | |
| 8,292,906 B2 | 10/2012 | Taylor et al. | |
| 8,313,509 B2 | 11/2012 | Kostrzewski | |
| 8,337,515 B2 | 12/2012 | Viola et al. | |
| 8,372,090 B2 | 2/2013 | Wingardner et al. | |
| 8,403,837 B2 | 3/2013 | Okoniewski | |
| 8,413,869 B2 | 4/2013 | Heinrich | |
| 8,465,499 B2 | 6/2013 | Onuki et al. | |
| 8,475,453 B2 | 7/2013 | Marczyk et al. | |
| 8,490,851 B2 | 7/2013 | Blier et al. | |
| 8,496,674 B2 | 7/2013 | Cabrera et al. | |
| 8,506,581 B2 | 8/2013 | Wingardner, III et al. | |
| 8,628,545 B2 | 1/2014 | Cabrera et al. | |
| 8,636,752 B2 | 1/2014 | Cabrera et al. | |
| 8,641,729 B2 | 2/2014 | Filipi et al. | |
| 8,721,640 B2 | 5/2014 | Taylor et al. | |
| 8,747,424 B2 | 6/2014 | Taylor et al. | |
| 8,882,785 B2 | 11/2014 | DiCesare et al. | |
| 8,906,041 B2 | 12/2014 | Chu | |
| 8,968,339 B2 | 3/2015 | Malkowski | |
| 8,968,340 B2 | 3/2015 | Chowaniec et al. | |
| 8,968,342 B2 | 3/2015 | Wingardner, III et al. | |
| 9,113,860 B2 | 8/2015 | Viola et al. | |
| 9,149,270 B2 | 10/2015 | Fogel | |
| 9,204,924 B2 | 12/2015 | Marczyk et al. | |
| 9,326,770 B2 | 5/2016 | Shelton, IV et al. | |
| 9,504,465 B2 | 11/2016 | Chu | |
| 10,231,729 B2 | 3/2019 | Sauer | |
| 10,390,818 B2 | 8/2019 | Keyser et al. | |
| 10,631,855 B2 | 4/2020 | Smith | |
| 10,660,637 B2 | 5/2020 | Taylor et al. | |
| 11,103,236 B2 | 8/2021 | Taylor et al. | |
| 2002/0038125 A1 | 3/2002 | Hamilton | |
| 2002/0119177 A1 | 8/2002 | Bowman et al. | |
| 2003/0208209 A1* | 11/2003 | Gambale | A61B 17/0482 606/144 |
| 2004/0015177 A1 | 1/2004 | Chu | |
| 2004/0034371 A1 | 2/2004 | Lehman et al. | |
| 2004/0158125 A1 | 8/2004 | Aznoian et al. | |
| 2004/0181238 A1 | 9/2004 | Zarbatany et al. | |
| 2004/0236353 A1 | 11/2004 | Bain et al. | |
| 2005/0154403 A1 | 7/2005 | Sauer et al. | |
| 2005/0251153 A1 | 11/2005 | Sakamoto et al. | |
| 2006/0036232 A1 | 2/2006 | Primavera et al. | |
| 2006/0047289 A1 | 3/2006 | Fogel | |
| 2006/0085016 A1 | 4/2006 | Eremia | |
| 2007/0021736 A1 | 1/2007 | Johnson | |
| 2007/0032801 A1 | 2/2007 | Pantages et al. | |
| 2007/0129735 A1* | 6/2007 | Filipi | A61B 17/320016 606/144 |
| 2007/0255296 A1* | 11/2007 | Sauer | A61B 17/30 606/144 |
| 2008/0147096 A1 | 6/2008 | Azonian et al. | |
| 2009/0018580 A1 | 1/2009 | Wulc | |
| 2009/0312775 A1 | 12/2009 | Gilkey et al. | |
| 2010/0016868 A1 | 1/2010 | Kim | |
| 2010/0137888 A1 | 6/2010 | Wulc et al. | |
| 2010/0249498 A1 | 9/2010 | Wingardner et al. | |
| 2011/0082347 A1 | 4/2011 | Okoniewski | |
| 2012/0016383 A1* | 1/2012 | Sauer | A61B 17/0483 606/144 |
| 2012/0029536 A1 | 2/2012 | Dicesare et al. | |
| 2012/0215235 A1 | 8/2012 | Fogel | |
| 2012/0221022 A1* | 8/2012 | Devens, Jr. | A61B 17/0469 606/144 |
| 2013/0035688 A1 | 2/2013 | Kerr et al. | |
| 2013/0172685 A1 | 7/2013 | Okoniewski | |
| 2013/0325058 A1* | 12/2013 | Roorda | A61B 17/06061 606/213 |
| 2014/0012292 A1 | 1/2014 | Stewart et al. | |
| 2014/0114309 A1 | 4/2014 | Payne et al. | |
| 2014/0163375 A1 | 6/2014 | Wasielewski | |
| 2014/0371760 A1 | 12/2014 | Menn | |
| 2015/0257751 A1 | 9/2015 | Bachar et al. | |
| 2015/0282805 A1 | 10/2015 | Sauer | |
| 2015/0359531 A1* | 12/2015 | Sauer | A61B 17/0469 606/148 |
| 2016/0213228 A1 | 7/2016 | Rohl et al. | |
| 2016/0338691 A1 | 11/2016 | Weber et al. | |
| 2017/0020510 A1 | 1/2017 | Skinlo et al. | |
| 2017/0095363 A1 | 4/2017 | Hiernaux et al. | |
| 2019/0307445 A1 | 10/2019 | Taylor et al. | |

FOREIGN PATENT DOCUMENTS

| | | |
|---|---|---|
| EP | 3 297 540 A1 | 3/2018 |
| EP | 3572005 A2 | 11/2019 |
| JP | 2005-296644 | 10/2005 |
| JP | 2006-512108 | 4/2006 |
| JP | 2011-528949 | 12/2011 |
| WO | 2004/062466 | 7/2004 |
| WO | WO 2006/023975 A2 | 3/2006 |
| WO | WO 2017/075309 A1 | 5/2017 |

OTHER PUBLICATIONS

PCT International Patent Application No. PCT/US18/21942, International Search Report and Written Opinion of the International Searching Authority dated May 24, 2018, 13 pages.

PCT International Patent Application No. PCT/US18/27173, International Search Report and Written Opinion of the International Searching Authority dated Jun. 29, 2018, 8 pages.

PCT International Patent Application No. PCT/US18/37406, International Search Report and Written Opinion of the International Searching Authority dated Sep. 13, 2018, 10 pages.

Boston Scientific. Capio™ SLIM Suture Capturing Device. Website https://www.bostonscientific.com/capio-slim/pdf, originally downloaded Apr. 14, 2021, 4 pages.

U.S. Appl. No. 15/947,612, Office Action mailed Dec. 11, 2019.

U.S. Appl. No. 15/947,612, Office Action mailed Jan. 14, 2020.

(56) References Cited

OTHER PUBLICATIONS

U.S. Appl. No. 15/994,932, Office Action mailed Mar. 4, 2020.
U.S. Appl. No. 15/917,217, Office Action mailed Sep. 18, 2019.
U.S. Appl. No. 15/917,217, Office Action mailed Mar. 18, 2020.
U.S. Appl. No. 15/994,932, Office Action mailed Jul. 21, 2020.
Japanese Patent Application No. 2021-503693, Office Action mailed Jan. 19, 2022, 10 pages (with English translation).
European Patent Application No. 18920964.6, Extended European Search Report dated Jan. 27, 2022, 10 pages.
Japanese Patent Application No. 2020-566288, Official Action mailed Feb. 16, 2022, 13 pages (with English translation).
European Patent Application N. 18913691.4, Supplementary Partial European Search Report mailed Dec. 12, 2021, 15 pages.
Israeli Patent Application No. 289477, Official Action dated Jul. 14, 2022, 6 pages.
Covidien. SILS™ Stitch Articulating Suturing Device. Product Sheet, www.covidiet.com, originally downloaded Jan. 6, 2016, 2 pages.
Covidien. V-Loc™ Wound Closure Reload For Use With Endo Stitch™ and SILS™ Stitch Suturing Devices. Product Sheet, www.covidiet.com, originally downloaded Jan. 6, 2016, 28 pages.
Eremia et al. Novel Face-Lift Suspension Suture and Inserting Instrument: Use of Large Anchors Knotted into a Suture with Attached Needle and Inserting Device Allowing for Single Entry Point Placement of Suspension Suture. Preliminary Report of 20 Cases with 6-to 12-Month Follow-Up. Dermatol Surg., Mar. 2006, 32(3):335-45.
PCT International Patent Application No. PCT/US07/21449, filed Oct. 5, 2007.
U.S. Appl. No. 60/958,474, filed Jul. 6, 2007.
U.S. Appl. No. 60/923,980, filed Apr. 17, 2007.
U.S. Appl. No. 60/923,804, filed Apr. 16, 2007.
U.S. Appl. No. 60/849,561, filed Oct. 5, 2006.
U.S. Appl. No. 60/849,508, filed Oct. 5, 2006.
U.S. Appl. No. 60/849,562, filed Oct. 5, 2006.
U.S. Appl. No. 62/473,271, filed Mar. 17, 2017.
U.S. Appl. No. 15/917,217, filed Mar. 9, 2018.
PCT International Patent Application No. PCT/US18/21942, filed Mar. 12, 2018.
U.S. Appl. No. 15/947,612, filed Apr. 6, 2018.
PCT International Patent Application No. PCT/US18/27173, filed Apr. 11, 2018.
U.S. Appl. No. 63/022,632, filed May 11, 2020.
European Patent Application No. 18913691.4, Extended European search Report dated Feb. 8, 2022, 15 pages.
Canadian Patent Application No. 3,096,018, Examination Office Action dated May 18, 2023, 3 pages.
Australian Patent Application No. 2018417948, Examination Report No. 1, dated Apr. 26, 2023, 3 pages.
Japanese Patent Application No. 2022-176182, Official Action mailed Sep. 26, 2023, 11 pages (with English translation).
Japanese Patent Application No. 2022-564747, Official Action mailed Dec. 1, 2023, 10 pages (with English translation).
Chinese Patent Application No. 201880093578.2, Office Action dated 2023-12-26, 19 pages (with English translation).
U.S. Appl. No. 17/143,388, Office Action dated Jan. 29, 2024.
U.S. Appl. No. 17/405,842, Office Action dated Feb. 22, 2024.
PCT International Patent Application No. PCT/US23/81177, International Search Report and Written Opinion of the International Searching Authority mailed Apr. 15, 2024, 8 pages.

\* cited by examiner

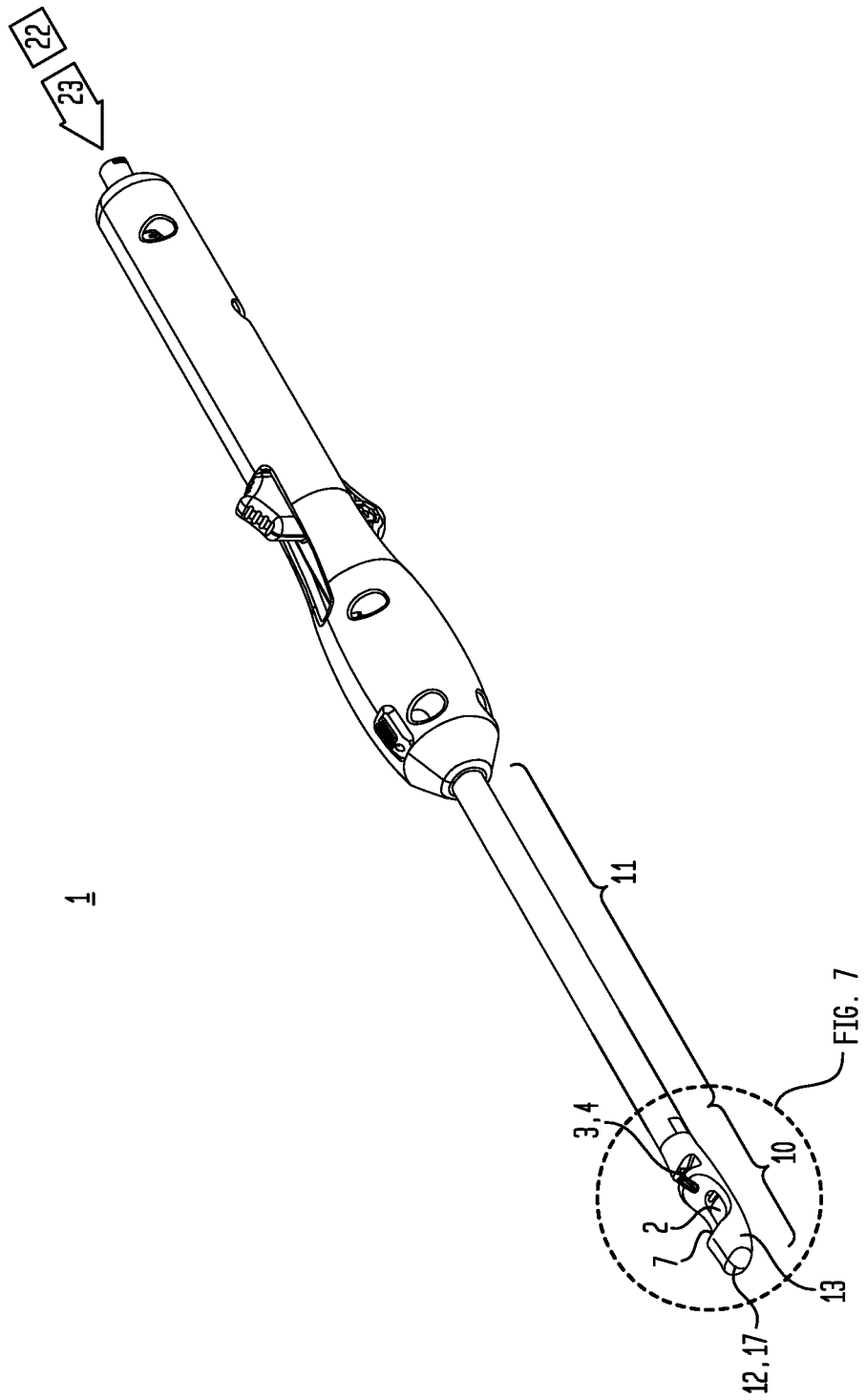

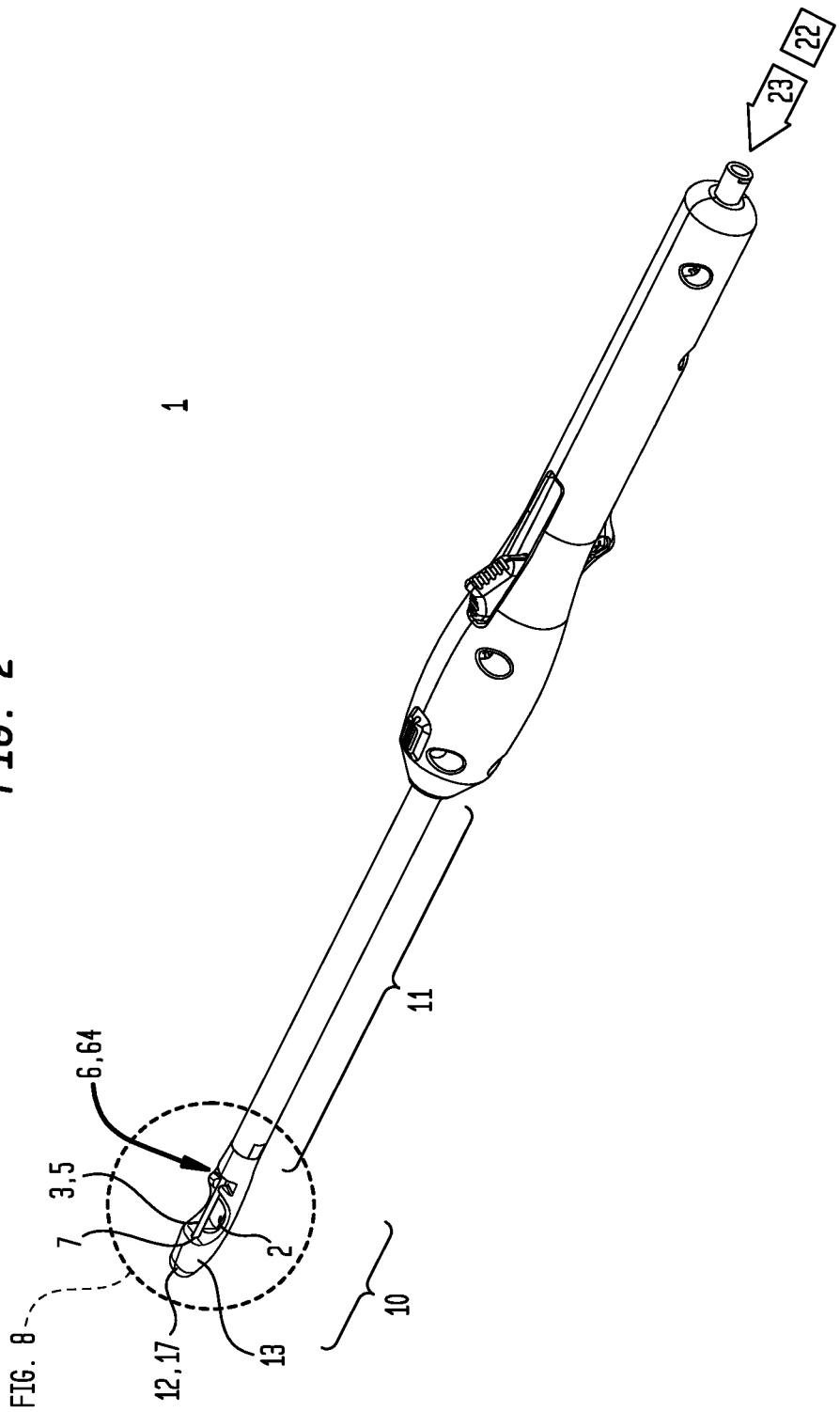

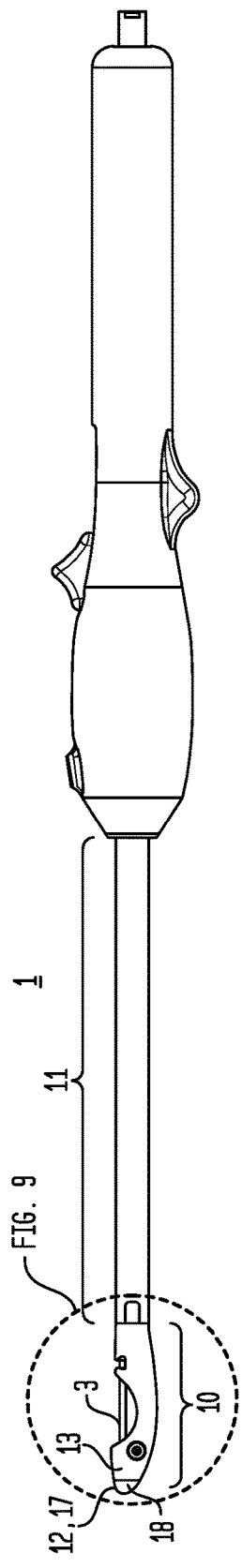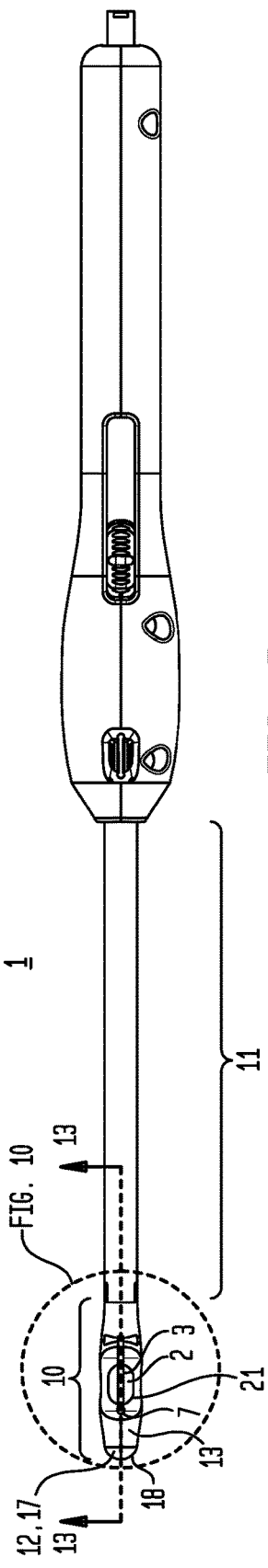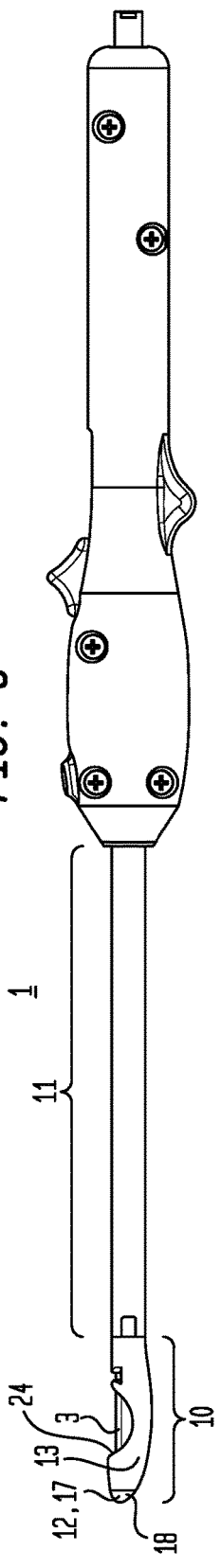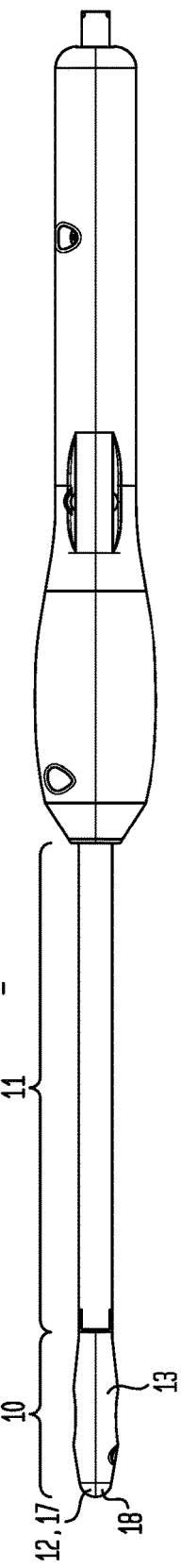

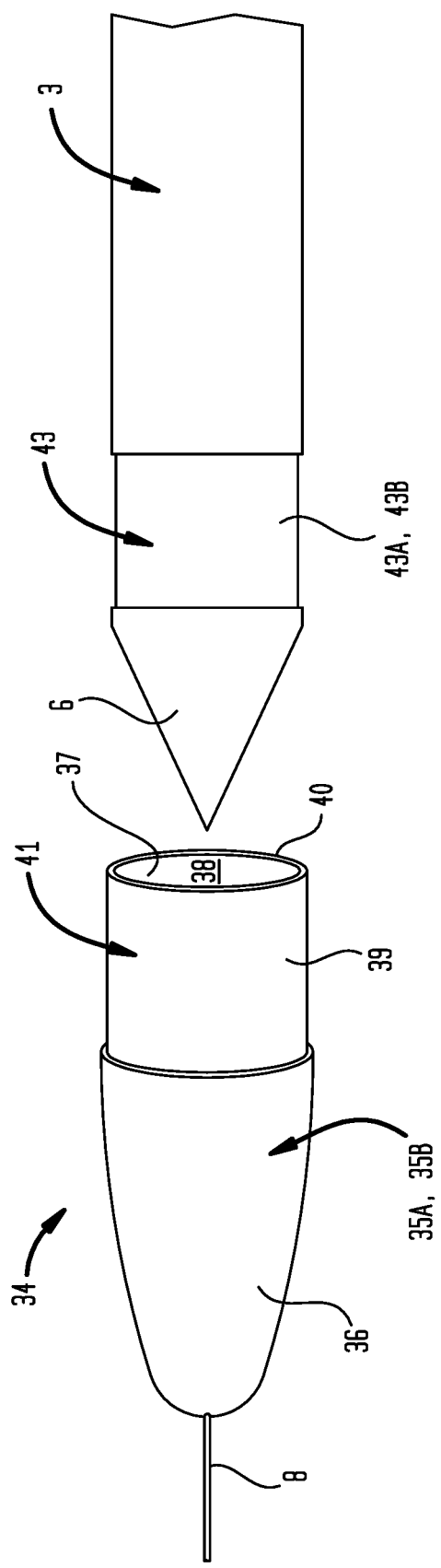

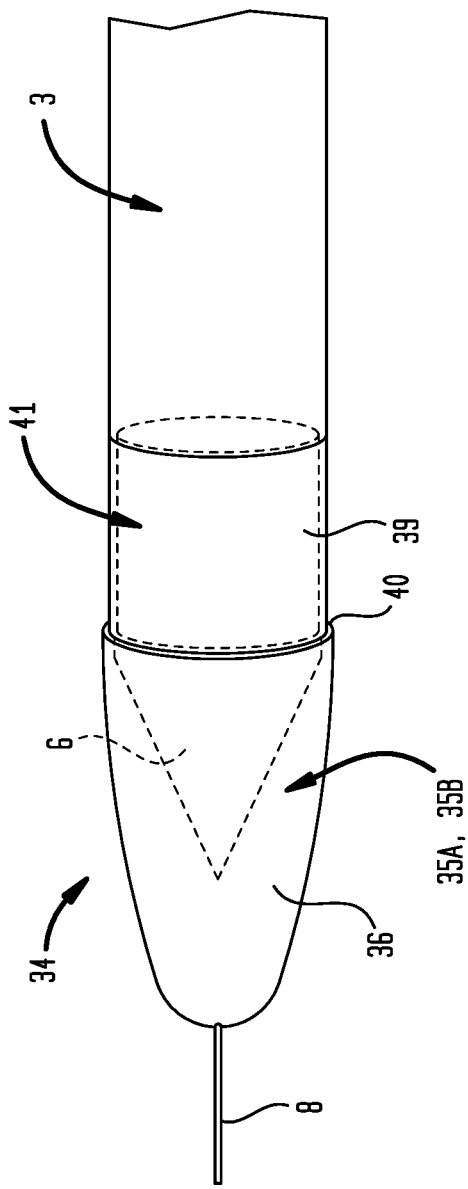

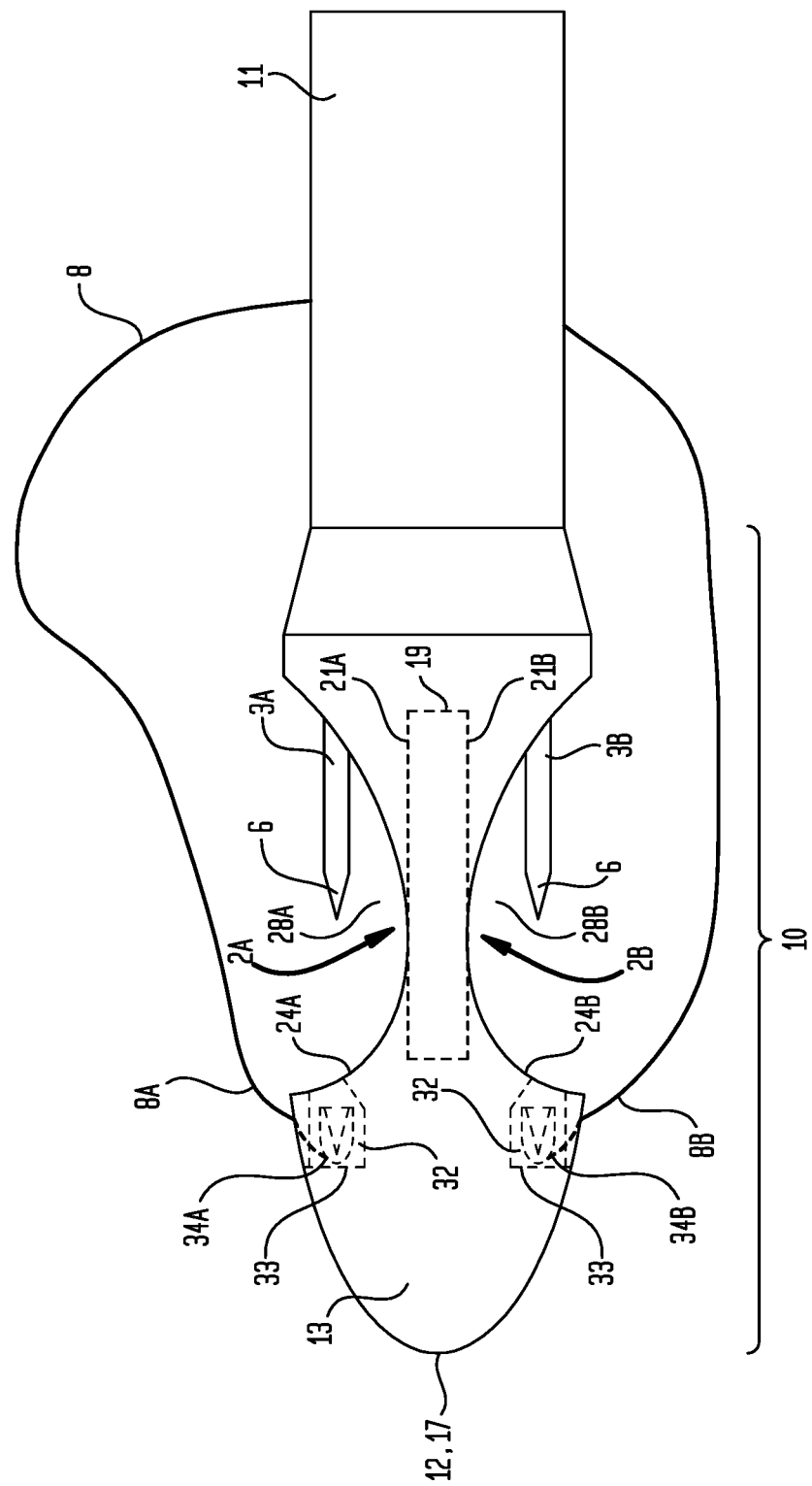

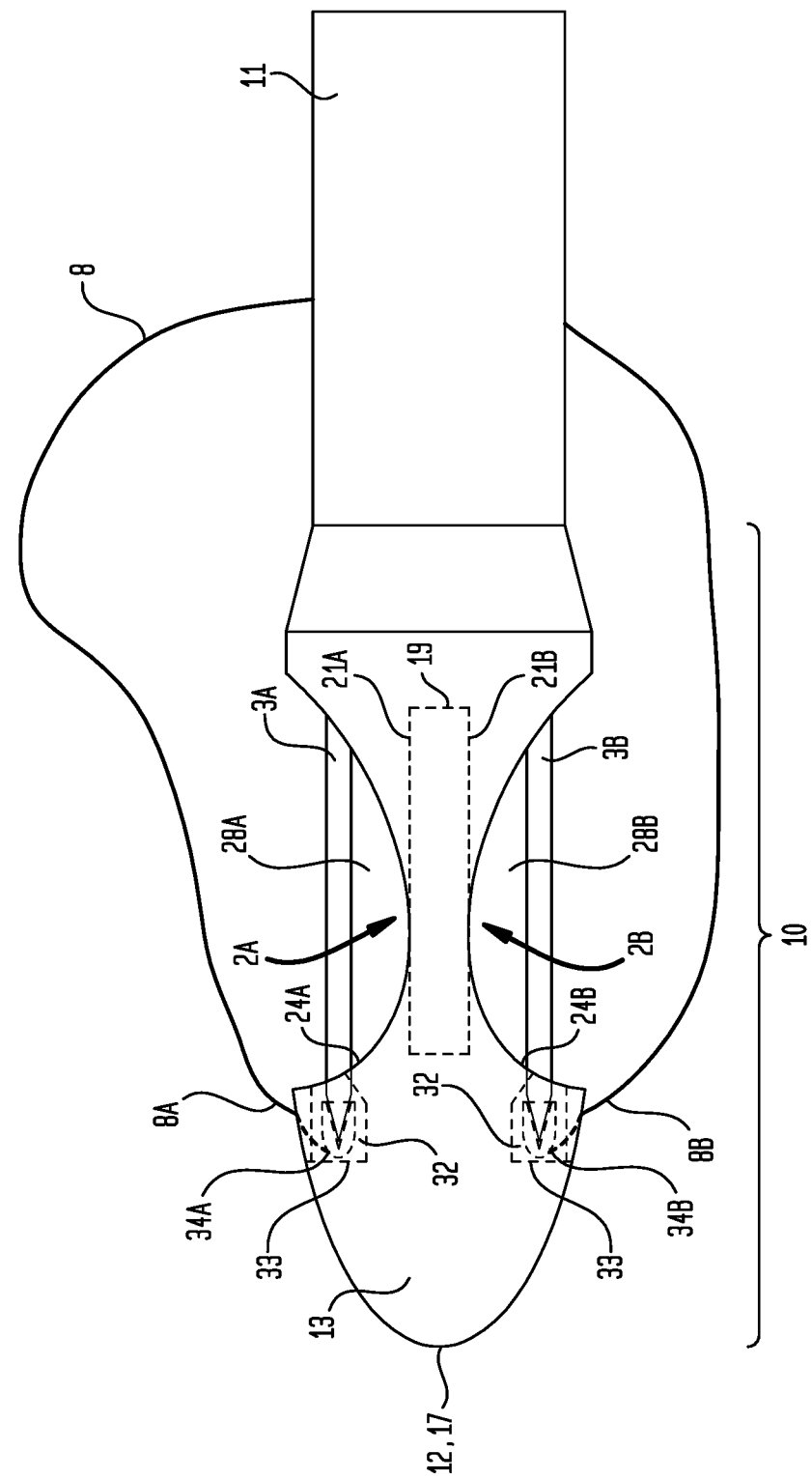

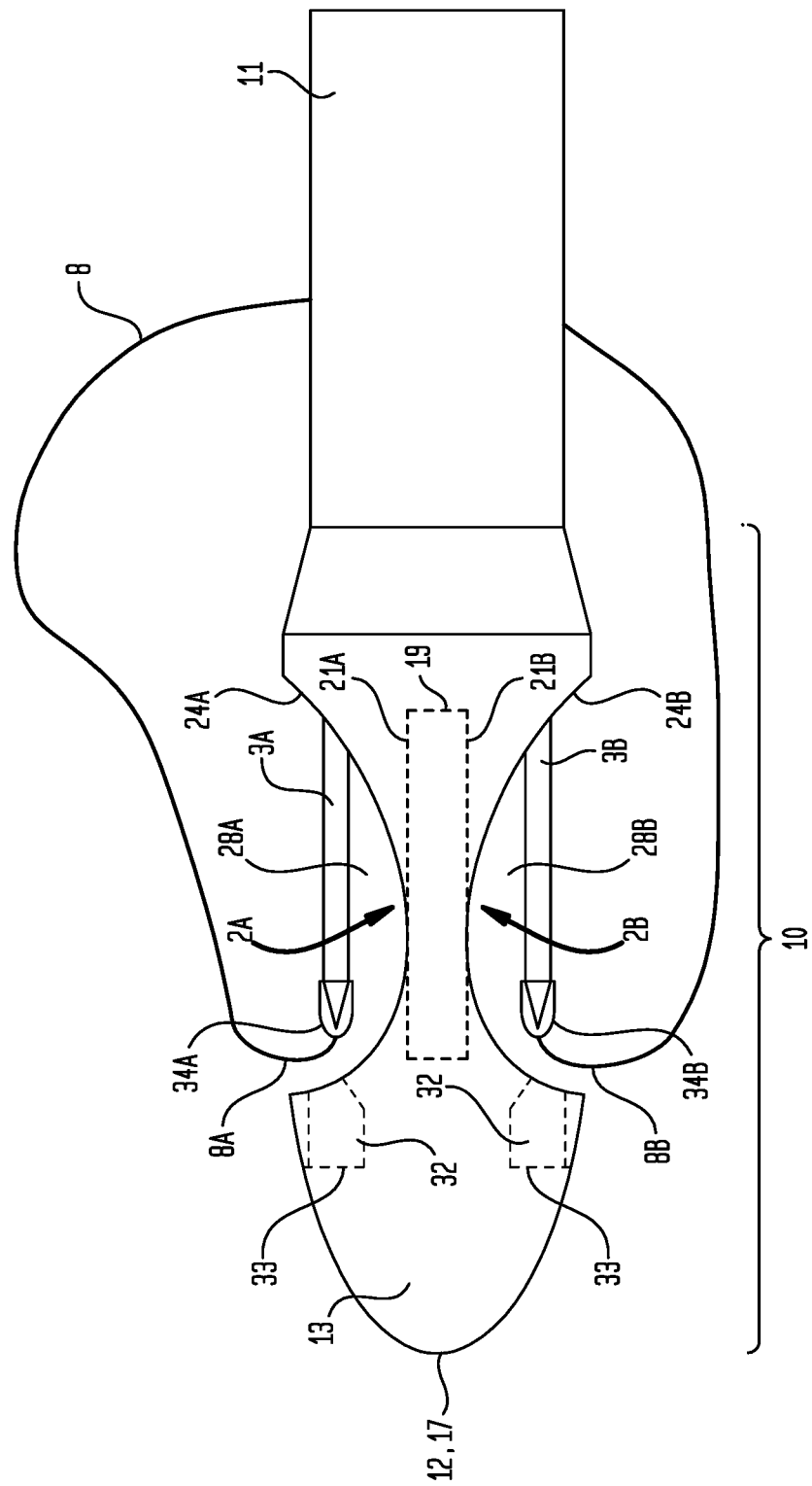

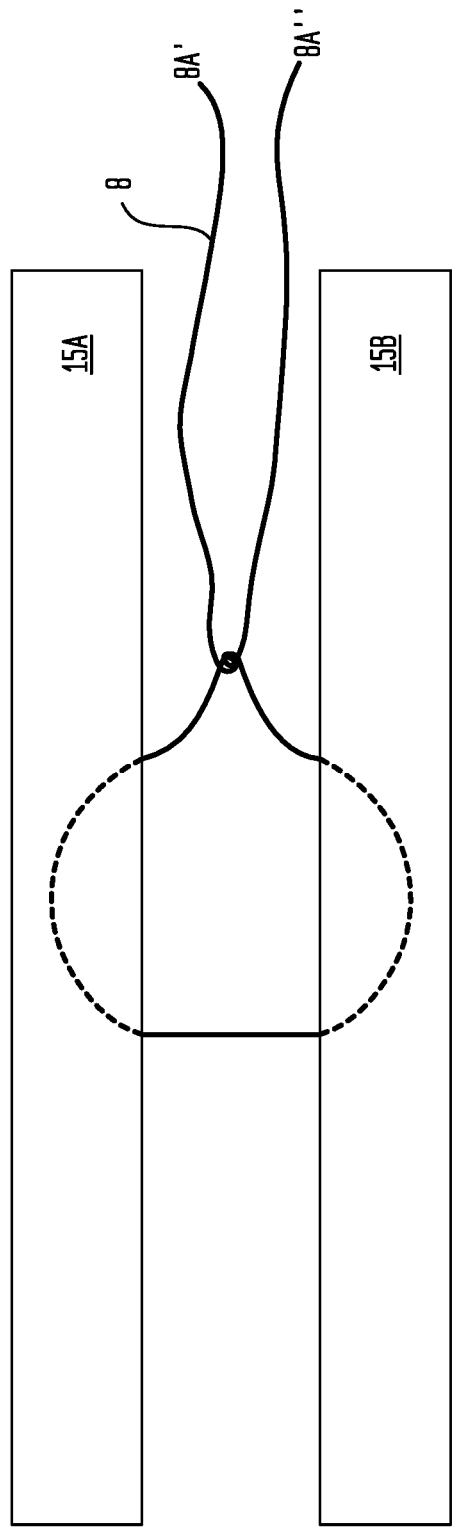

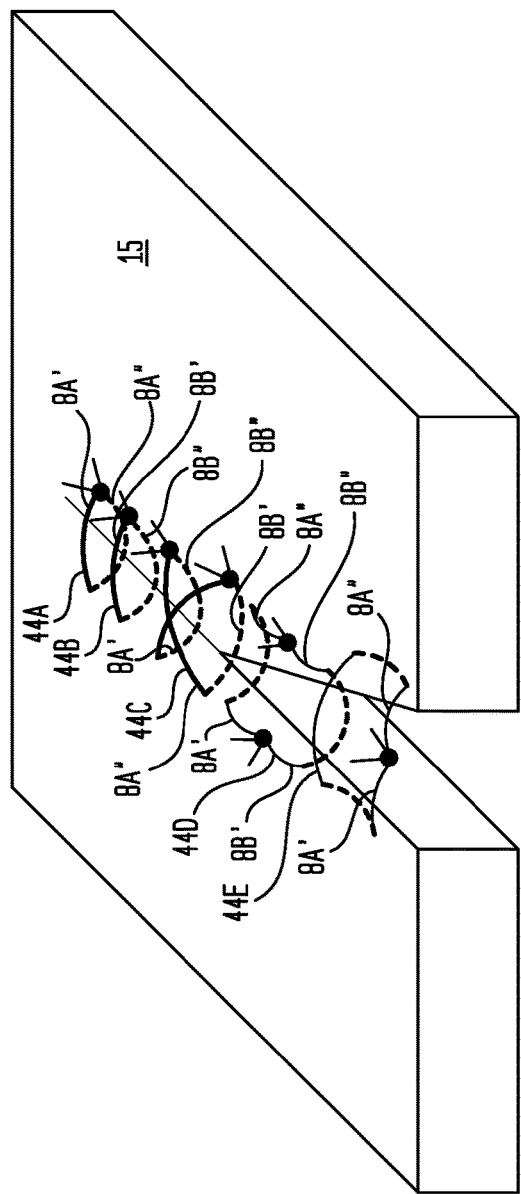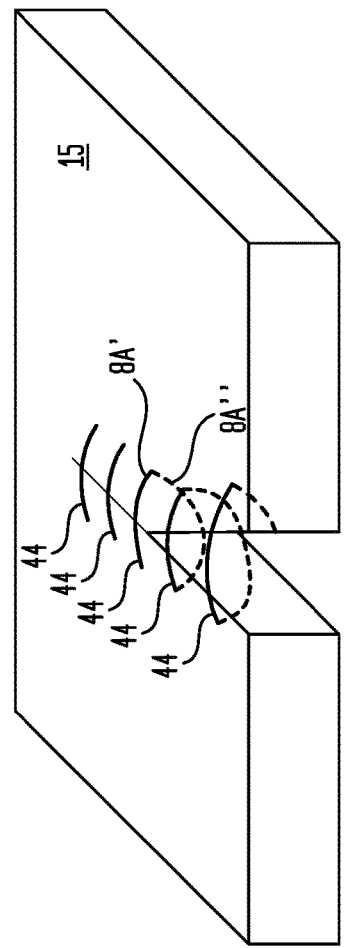

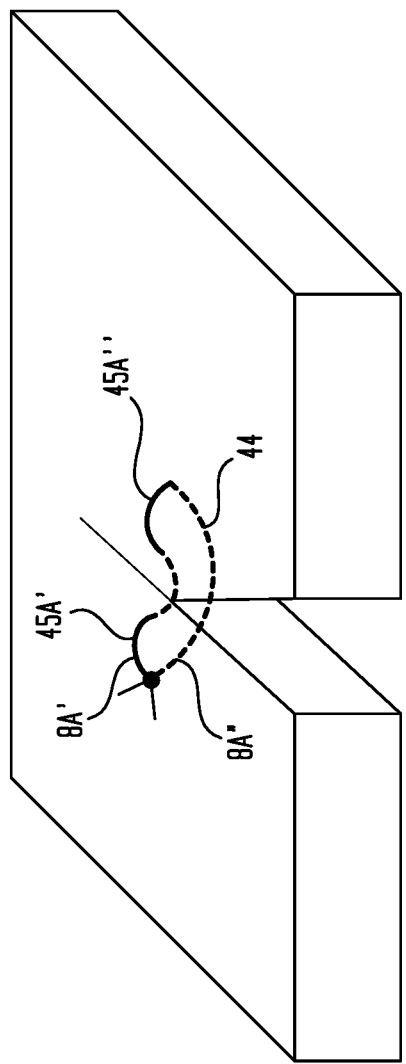

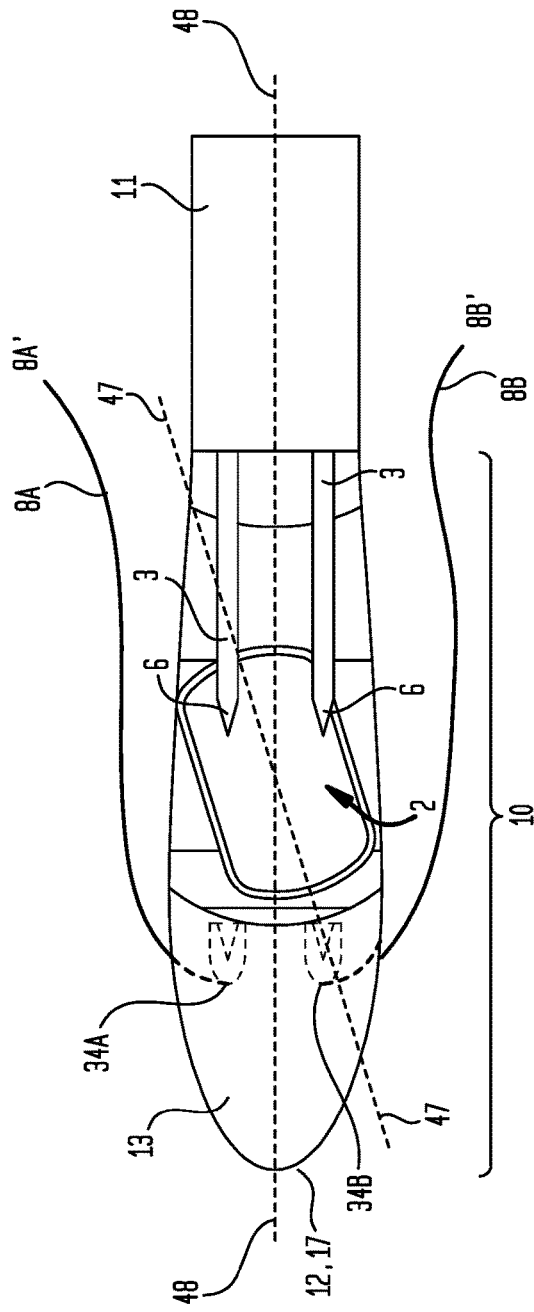

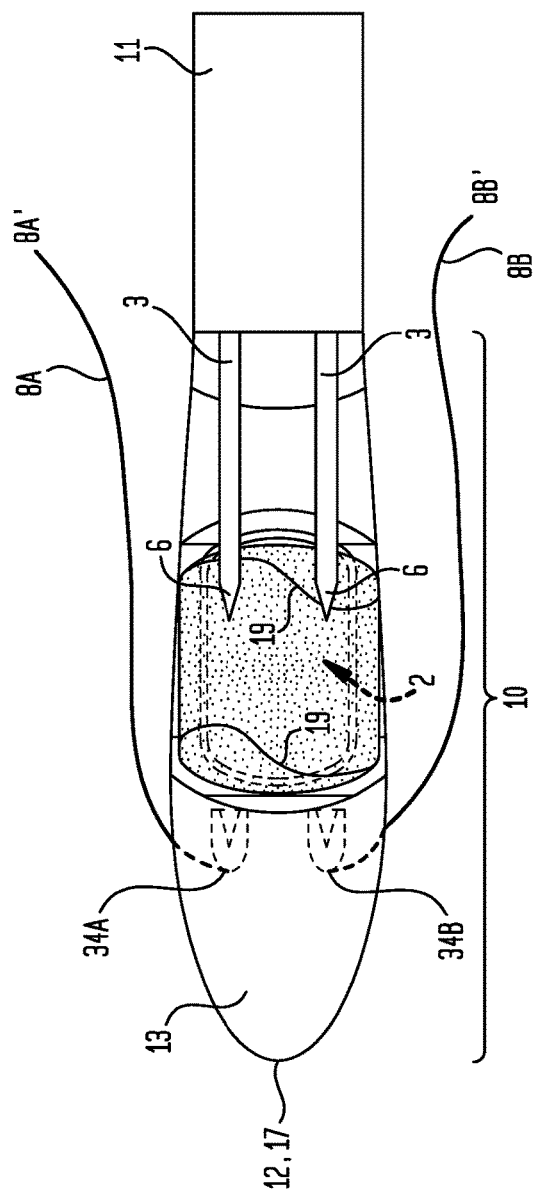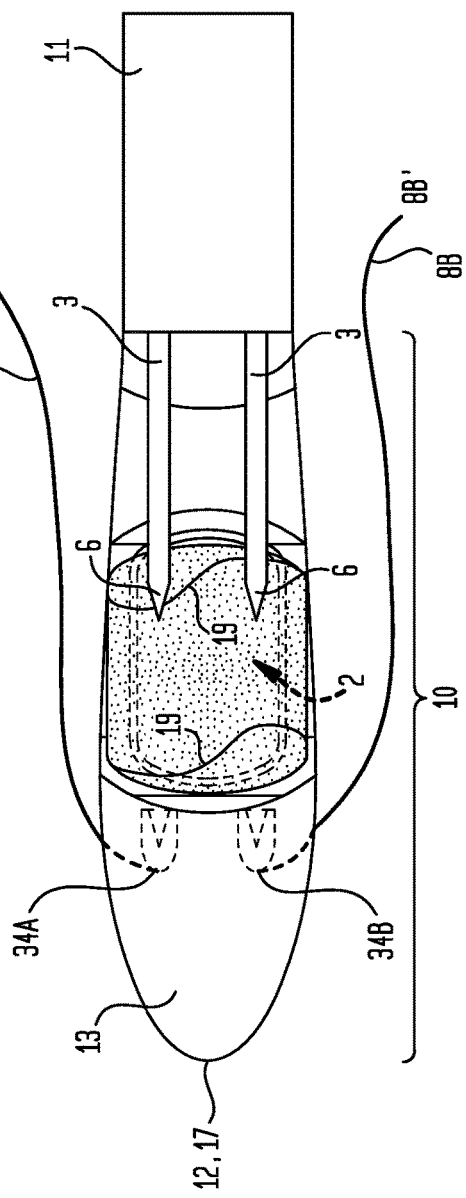

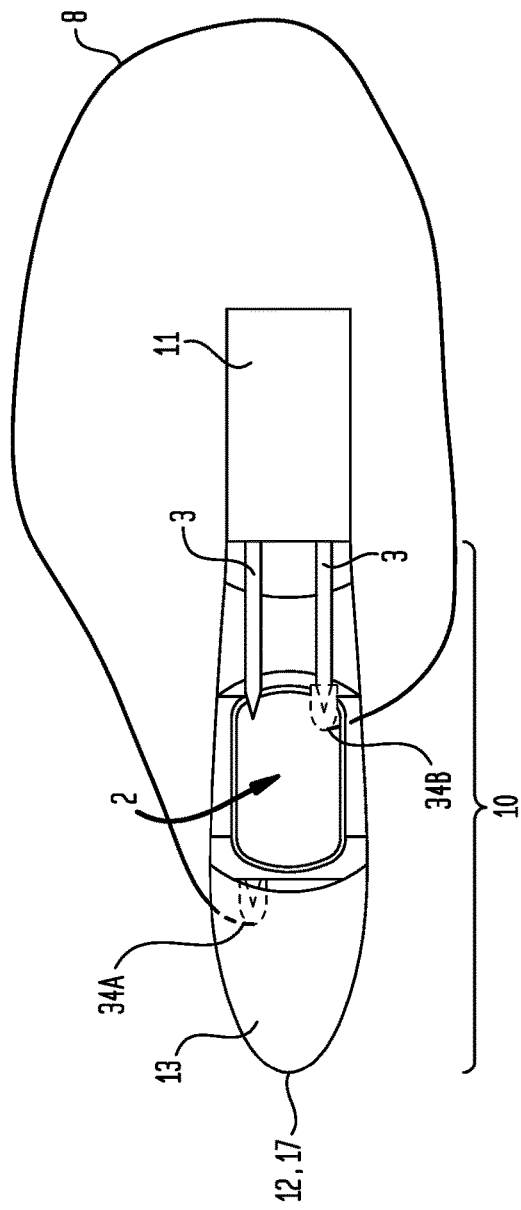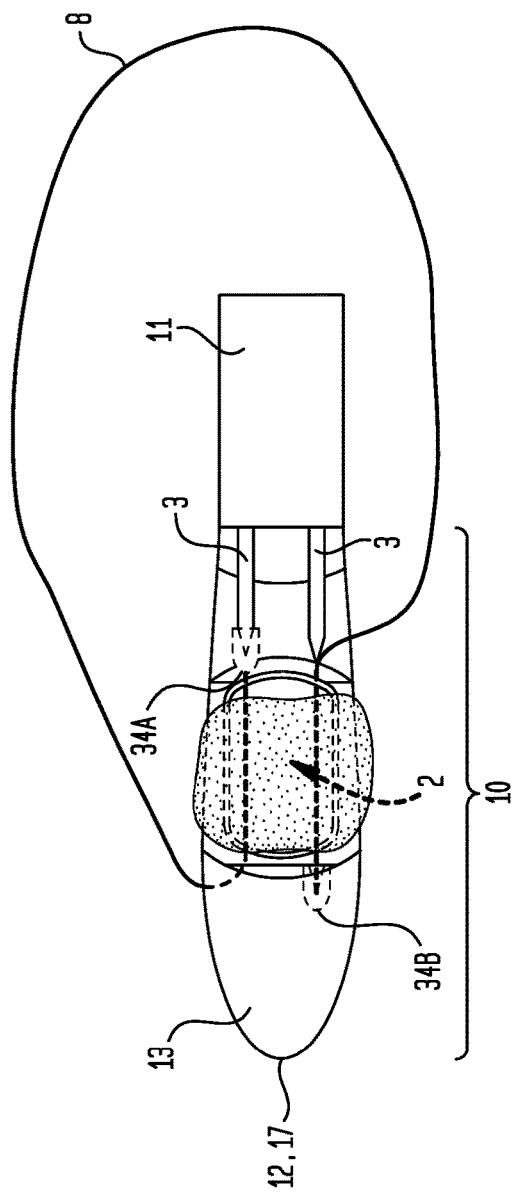

MULTIPLE SUTURE PLACEMENT SYSTEM

I. FIELD OF THE INVENTION

A suturing system including apparatus and methods for disposing sutures in a substrate.

II. SUMMARY OF THE INVENTION

Accordingly, a broad object of particular embodiments of the present invention can be to provide an apparatus including a suturing probe having a suturing probe recessed external surface delimiting an open recessed area with a thread capture chamber opening into said open recessed area of said suturing probe recessed external surface and a substrate capture chamber having a chamber side wall extending from a chamber bottom to a chamber port defining a transition edge delimiting a substrate chamber entry in said open recessed area of said suturing probe recessed external surface and a thread carrier passage opening into said open recessed area of said suturing probe recessed external surface, whereby a thread carrier slidably engaged in said thread carrier passage can extend from said thread carrier passage into said thread capture chamber within an open space defined by of said open recessed area while remaining outside of said substrate capture chamber.

Another broad object of particular embodiments of the present invention can be to provide a suturing probe including a thread capture chamber having a thread lappet receiver configured to removably retain a thread lappet and a substrate capture chamber disposed adjacent to said thread capture chamber, said substrate capture chamber having a chamber port open to a suturing probe external surface, and a thread carrier slidingly engaged to said suturing probe, wherein extension of said thread carrier moves said thread carrier into said thread lappet receiver of said thread capture chamber, said thread carrier configured to mateably engage said thread lappet to carry said thread lappet to or from said thread lappet receiver.

Another broad object of particular embodiments of the present invention can be to provide a suturing probe including first and second suturing probe recessed external surfaces correspondingly delimiting in outward opposite facing relation a first open recessed area and a second open recessed area, a pair of thread capture chambers correspondingly opening into said first and second open recessed areas of said suturing probe recessed external surface, a substrate capture chamber having a chamber side wall and first and second chamber ports each defining a transition edge correspondingly delimiting a substrate chamber entry in said first and second open recessed areas of said suturing probe recessed external surface, a pair of thread carrier passages one opening into each of said first and second open recessed areas of said suturing probe recessed external surface, and a pair of thread carriers correspondingly slidably engaged in said pair thread carrier passages, each of said pair thread carriers correspondingly extendable from said pair thread carrier passages within first and second open spaces defined by said first and second open recessed areas and outside of said substrate capture chamber into a corresponding one of said pair thread capture chambers.

Naturally, further objects of the invention are disclosed throughout other areas of the specification, drawings, photographs, and claims.

III. A BRIEF DESCRIPTION OF THE DRAWINGS

FIG. 1 is a first perspective view of an embodiment of the suturing apparatus having a thread carrier in a retracted condition.

FIG. 2 is a second perspective view of an embodiment of the suturing apparatus having the thread carrier in an extended condition.

FIG. 3 is a first side elevation view of an embodiment of the suturing apparatus.

FIG. 4 is a top plan view of an embodiment of the suturing apparatus.

FIG. 5 is a second side elevation view of an embodiment of the suturing apparatus.

FIG. 6 is a bottom plan view of an embodiment of the suturing apparatus.

FIG. 14 illustrates an embodiment of a thread lappet having an extending thread and a thread carrier terminal end including an embodiment of a thread lappet capture element.

FIG. 15 illustrates the thread carrier terminal end slidably engaged with the embodiment of the thread lappet shown in FIG. 14.

FIG. 25 is a top plan view of an embodiment of the suturing probe having a pair of extendable thread carriers correspondingly slidably engaged in the suturing apparatus to pass within a pair of recessed portions of the suturing probe.

FIG. 26 is a top plan view of an embodiment of the suturing probe having a pair of extendable thread carriers correspondingly slidably engaged in the suturing apparatus to pass within a pair of recessed portions of the suturing probe and correspondingly engage a pair of thread lappets.

FIG. 27 is a top plan view of an embodiment of the suturing probe having a pair of extendable thread carriers correspondingly slidably engaged in the suturing apparatus to pass within a pair of recessed portions of the suturing probe and correspondingly draw a pair of thread lappets through the pair of recessed portions of the suturing probe.

FIG. 28 is an illustration of a thread disposed in a pair of substrates by operation of the embodiment of the suturing probe shown in FIGS. 25 through 27.

FIG. 29 is an illustration of a plurality of sutures disposed in a substrate by joining the opposite pair of thread ends of each thread passed through the substrate by operation of embodiments of the suturing probe.

FIG. 30 is an illustration of a continuous suture disposed in a substrate by joining the first thread end of a first thread with the second thread end of a second thread passed through the substrate by operation of embodiments of the suturing probe.

FIG. 31 is an illustration of a suture disposed in a substrate by drawing the pair of thread ends of one tread through the substrate by operation of embodiments of the suturing probe and joining the thread first and second ends.

FIG. 32A is a top plan view of an embodiment of the suturing probe having a substrate capture chamber disposed in angled relation to the longitudinal axis of the suturing probe.

FIG. 32B is a top plan view of an embodiment of the suturing probe having a substrate capture chamber disposed in angled relation to the longitudinal axis of the suturing probe.

FIG. 33A is a top plan view of an embodiment of the suturing probe having a substrate capture chamber side will configured to urge a captured substrate into a desired spatial relation to the path of the thread carrier.

FIG. 33B is a top plan view of an embodiment of the suturing probe having a substrate capture chamber side will configured to urge a captured substrate into a desired spatial relation to the path of the thread carrier.

FIG. 36A is a top plan view of an embodiment of the suturing probe having a first of a pair of lappet bodies coupled to a thread carrier terminal end of a first of a pair of thread carriers, and the second of the pair of lappet bodies mounted to a thread lappet receiver of the thread capture chamber.

FIG. 36B is a top plan view of an embodiment of the suturing probe which upon extension of the pair of thread carriers shown in FIG. 36A drives the first of the pair of lappet bodies mounted on the thread carrier terminal end of the first thread carrier through a captured substrate, while the second lappet body mounted to the thread lappet receiver engages the thread carrier terminal end of the second thread carrier and retraction of the pair of thread carriers draws the second lappet body through the substrate.

Figure 37A:
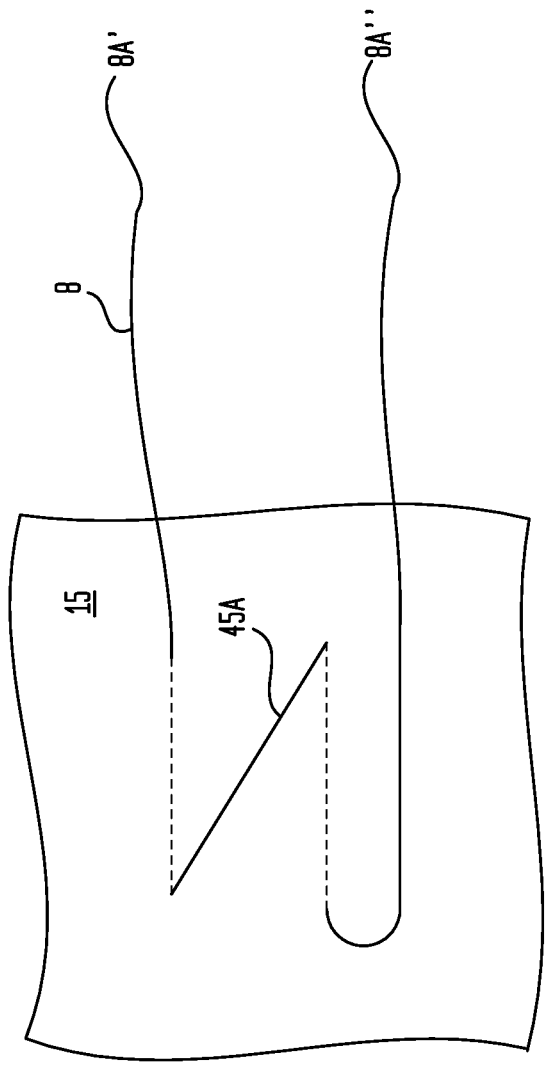

FIG. 37A is an illustration of the path of the thread in the substrate resulting from the method shown in FIGS. 36A and 36B.

Figure 37B:
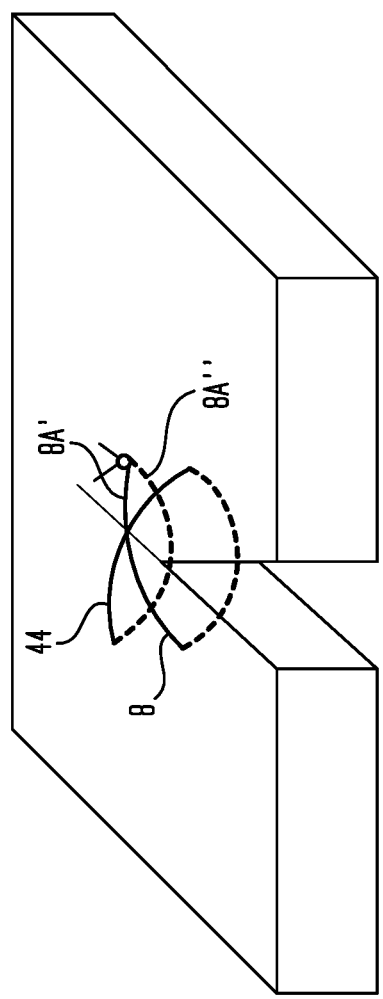

FIG. 37B is an illustration of the suture in the substrate resulting from joining the opposite thread ends of the thread passed through the substrate as shown in FIG. 37A.

Figure 38:
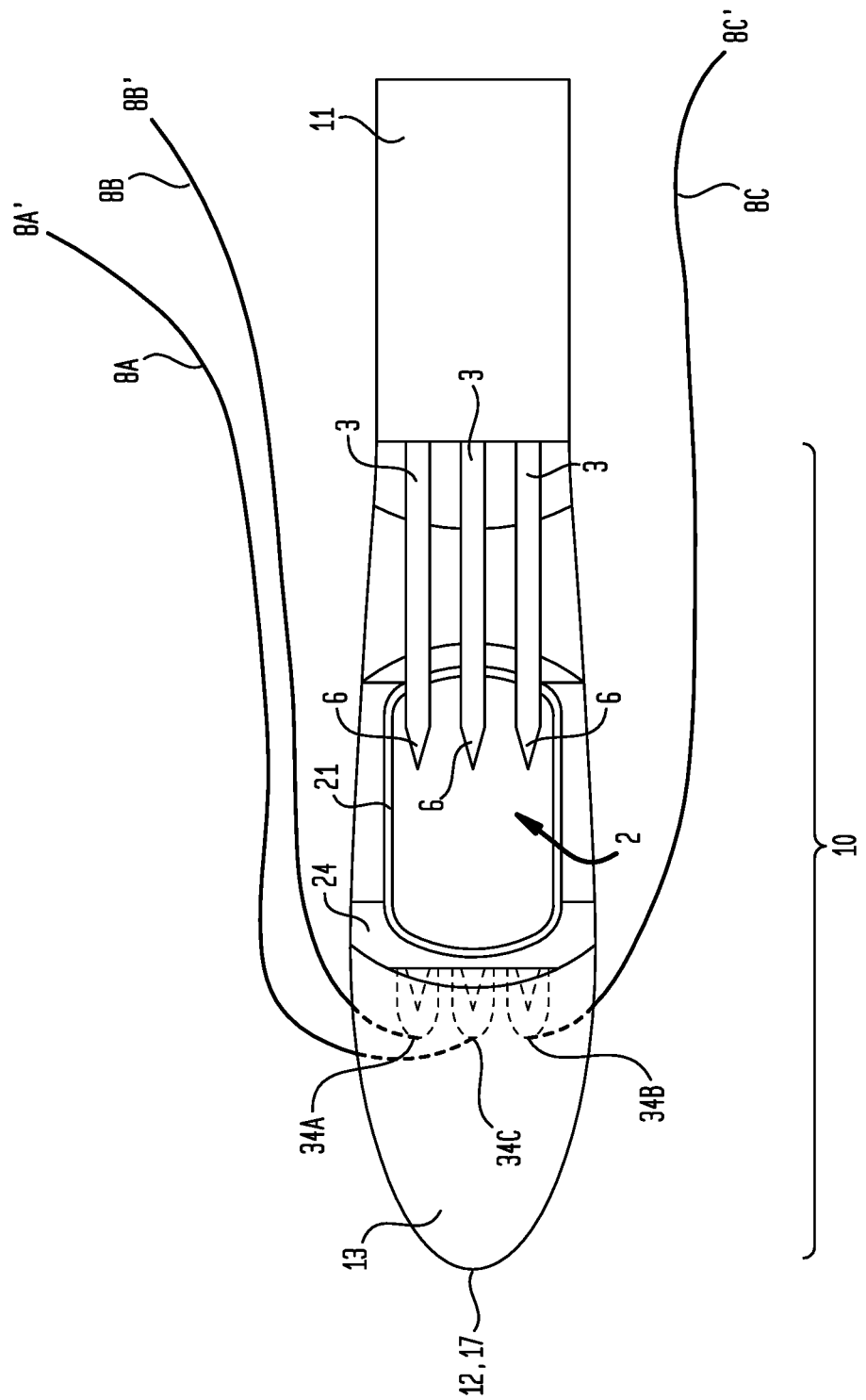

FIG. 38 is a top plan view of an embodiment of the suturing probe having three thread carriers slidably engaged in the suturing apparatus to pass within the recessed portion of the suturing probe.

IV. DETAILED DESCRIPTION OF THE PREFERRED EMBODIMENTS

Now, with general reference to FIGS. 1 through 10 and 11A through 11E, which provide illustrative examples of a suturing apparatus (1)(as shown in the examples of FIGS. 1 through 10) and methods using the suturing apparatus passing a thread (8) through a substrate (15) (as shown by the examples of FIGS. 11A through 11E). Embodiments of a suturing apparatus (1) can include a substrate capture chamber (2) and a thread carrier (3) which axially moves between a retracted condition (4) toward an extended condition (5) in which a thread carrier terminal end (6) of the thread carrier (3) passes outside of the substrate capture chamber (2) into a thread capture chamber (7) to either deliver a thread (8) to or retrieve thread (8) from a thread capture chamber (7) to dispose the thread in the substrate (15).

Now, with reference to FIGS. 7 through 10 and 11A through 11E, embodiments of the suturing apparatus (1) can include a suturing probe (10). The suturing probe (10) can outward axially extend from a tubular member (11) to terminate in a probe tip (12). The suturing probe external surface (13) can, but need not necessarily, be configured as an extension of the external dimensions of the tubular member (11) allowing the probe tip (12) to pass through body openings (14) such as natural body openings or incisions to engage a substrate (15) (as shown in the illustrative example of FIGS. 11A through 11E) such as skin, fascia, fat, or muscle. While particular examples of a substrate (15) include tissue (16) including human or animal tissue, this description is not intended to preclude the capture of substrates (15) other than human or animal tissue, including as illustrative examples, cadaver tissue, simulants of tissue, tissue models, elastomer components, plastic or natural fabrics, or the like.

Again, with reference to FIGS. 1 through 10 and 11A through 11E, in particular embodiments, the suturing probe (10) can have a generally cylindrical suturing probe external surface (13) terminating in a hebetated probe tip (17). As to particular embodiments, the suturing probe external surface (13) can include a tapered, beveled, or sloped surface approaching the probe tip (17) to reduce dimensions at the probe tip (17). There can be an advantage in having a sloped, tapered or inclined probe face (18) as it allows the suturing probe (10) additional ingress in relation to a substrate (15) such as animal tissues with a lesser amount of tissue dissection or trauma.

Again, with reference to FIGS. 1 through 10, in particular embodiments, a substrate capture chamber (2) can be disposed in the suturing probe (10). The substrate capture chamber (2) can include a chamber sidewall (19) which couples in opposed fixed relation a chamber bottom (20) a distance from a chamber port (21) open to the suturing probe external surface (13). In particular embodiments, the substrate capture chamber (2) can, but need not necessarily, be fluidically coupled to a vacuum source (22) operable to generate a reduction in a chamber pressure (23) in the substrate capture chamber (2) sufficient to capture, draw, or dispose a substrate (15) at the chamber port (21) or into the substrate capture chamber (2).

Now, with primary reference to FIGS. 7 through 10, in particular embodiments, the suturing probe (10) can, but need not necessarily, include a suturing probe recessed external surface (24) extending to a recess transition boundary (24') which delimits an open recessed area (24") in the suturing probe external surface (13) defining a recess interior space (28). As shown in the illustrative examples, the chamber port (21) defines and transition edge between the chamber sidewall (19) and the open recessed area (24") delimiting a substrate capture chamber opening (2') surrounded by the open recessed area (24") of the suturing probe recessed external surface (24), whereby the chamber port can circumscribe a substrate capture chamber opening of lesser area then the open recessed area (24") delimited by the recess transition boundary (24'). The structural relationship between the substrate capture chamber (2) and the suturing probe recessed external surface (24) can confer a substantial advantage by allowing the substrate (15) to be captured by the substrate capture chamber (2) under a pressure (23) reduced as compared to the recessed interior space (28) within the suturing probe recessed external surface (24) which can remain at or near ambient pressure (29).

Figure 8:
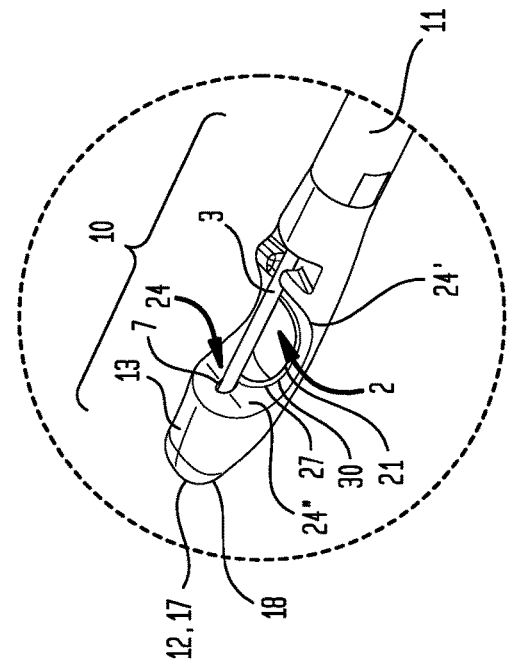
FIG. 8 is an enlarged view of the suturing probe shown FIG. 2.
Figure 7:
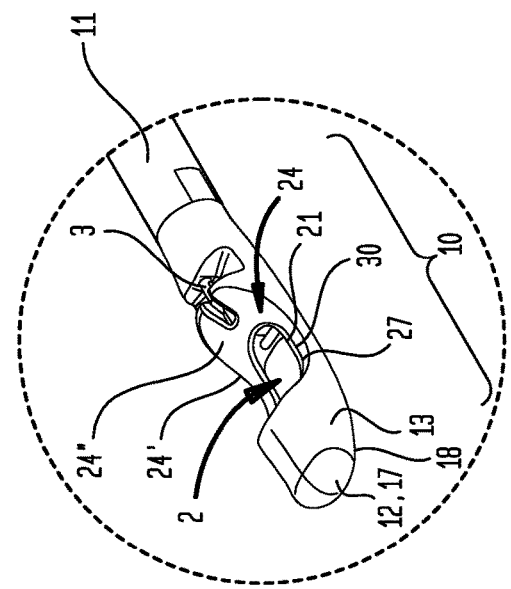
FIG. 7 is an enlarged view of the suturing probe shown in FIG. 1.
Figure 10:
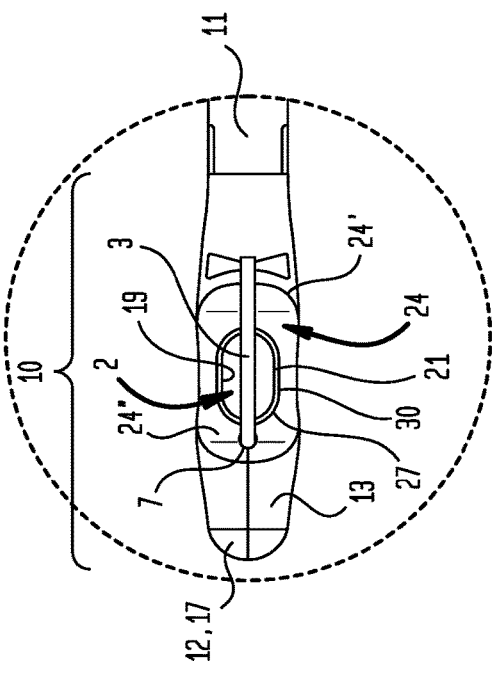
FIG. 10 is an enlarged view of the suturing probe shown in FIG. 4.
Figure 9:
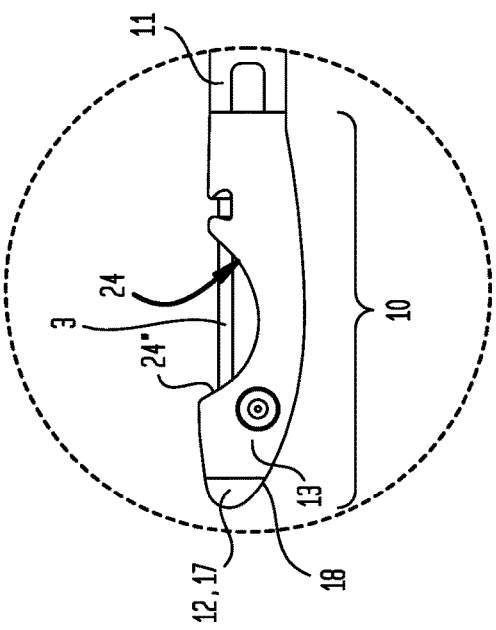
FIG. 9 is an enlarged view of the portion 9 shown in FIG. 3 side elevation view of a particular embodiment of a suturing probe.

Now, with primary reference to FIG. 10, in particular embodiments, the open recessed area (24") of the suturing probe external surface (13) can afford a substantially flat arcuate face (26) surrounding the chamber port (21). In particular embodiments, the chamber port (21) can, but need not necessarily, further provide a raised chamber port peripheral margin (27) which under reduced chamber pressure (23) in the substrate capture chamber (3) can assist in retaining the substrate (15) in the substrate capture chamber (2). In particular embodiments, the chamber port peripheral margin (27) can be raised above the level of the arcuate flat face (26) of the open recessed area (24") of the suturing probe external surface (13). This can, but need not necessarily, provide a chamber port peripheral margin (27) having less curvature than the arcuate flat face (26), or a chamber port peripheral margin (27) extending outward of the arcuate flat face (26) to terminate in a flattened peripheral margin face (30), or a combination thereof.

Figure 11C:
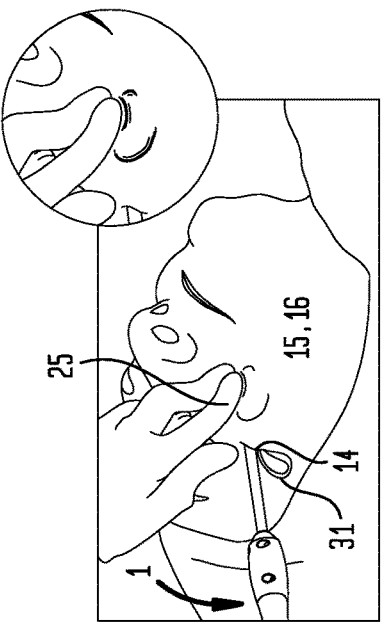
FIG. 11C is a depiction of a particular method of palpating a substrate toward a substrate capture chamber.
Figure 11B:
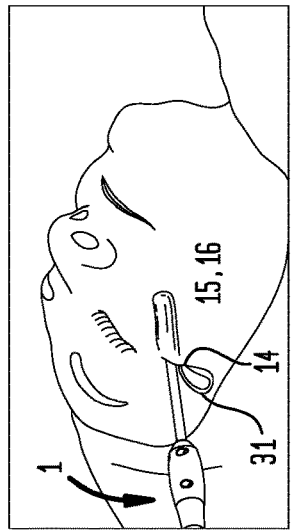
FIG. 11B is a depiction of a particular method of inserting a particular embodiment of a suturing probe in a body opening.
Figure 11A:
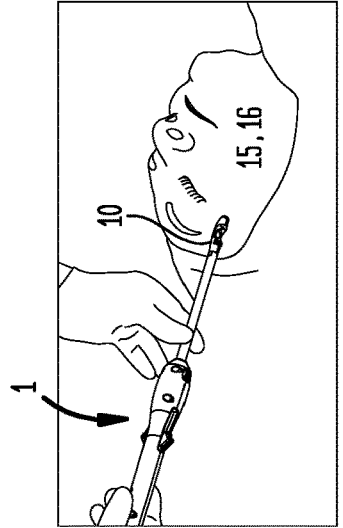
FIG. 11A is a depiction of a particular method of using a particular embodiment of a suturing apparatus.
Figure 11E:
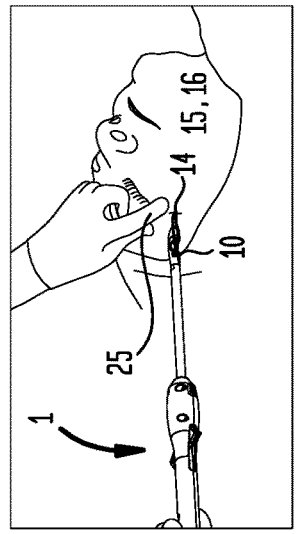
FIG. 11E is a depiction of a particular method of disposing thread loop in the substrate and removing a suturing probe from a body opening.
Figure 11D:
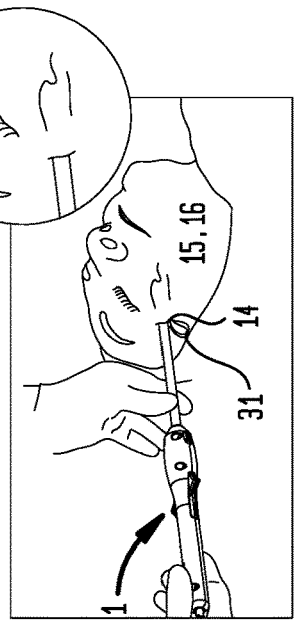
FIG. 11D is a depiction of a particular method of operating the suturing apparatus to drive the thread carrier through a substrate to dispose a thread in the substrate.

Again, with primary reference to FIGS. 1 through 10, one or more thread carriers (3) can be disposed to pass through the recessed interior space (28) of the open recessed area (24") outside of the substrate capture chamber (2). There can be substantial advantages in the structure of the suturing probe external surface (13) having both an open recessed area (24") and a substrate capture chamber (2) which opens to the open recessed area (24"). In the first instance, the recessed external surface (24) of the suturing probe external surface (13) can, but need not necessarily, be configured to allow a tip of a finger (25) to apply force to a substrate (15) to move the substrate toward the substrate capture chamber (2)(as shown in the example of FIG. 11C). In the second instance, the substrate capture chamber (2) under reduced pressure (23) can assist to capture and retain the substrate (15) while maintaining ambient or near ambient pressure (29) in the open recessed area (24") through which one or more thread carrier (3) can pass. Accordingly, while the substrate (15) can be retained at the chamber port (21) with the substrate capture chamber (2) under reduced chamber pressure (23), the thread carrier (3) can pass through the substrate (15) under ambient pressure (29) which avoids having body fluids (31) being drawn from the substrate (15), and further avoids having the body fluids (31) drawn into the tubular member (11) in which the tread carrier (3) extends and retracts.

Additionally, in particular embodiments, the chamber port peripheral margin (27) can increase the surface area of the suturing probe external surface (13) contacting a substrate (15). The increased surface area of the suturing probe external surface (13) can afford a substantial advantage in capture of a substrate (15) in those embodiments in which a reduced chamber pressure (22) can be generated in the substrate capture chamber (2) or can decrease movement of the suturing probe (10) in relation to substrate (15) captured in the substrate capture chamber (2).

Now with general reference to FIGS. 12 through 38, embodiments of the suturing probe (12) can include one thread carrier (3) as shown in the example of FIGS. 1 through 10, or can include a plurality of thread carriers (3) as shown in the examples of FIGS. 12 through 20 having two thread carriers (3), or the example of FIG. 38 having three thread carriers (3); however, these illustrative examples are not intended to preclude embodiments having a greater number of thread carriers (3).

Figure 12:
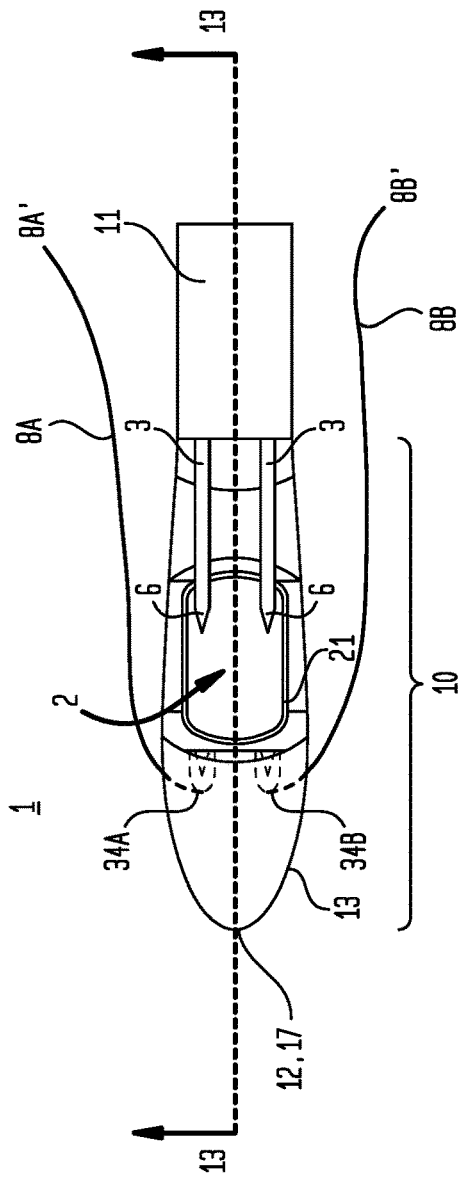
FIG. 12 is a top plan view of an embodiment of a suturing probe of the suturing apparatus having a plurality of thread carriers.
Figure 13:
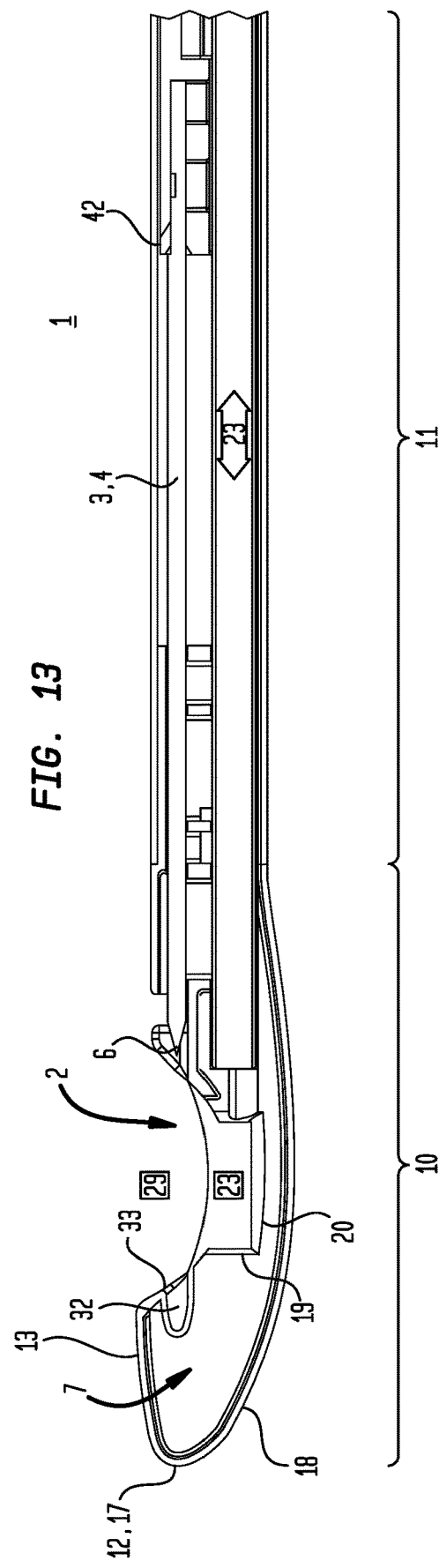
FIG. 13 is a cross section view 13-13 shown in FIG. 12.
Figure 17:
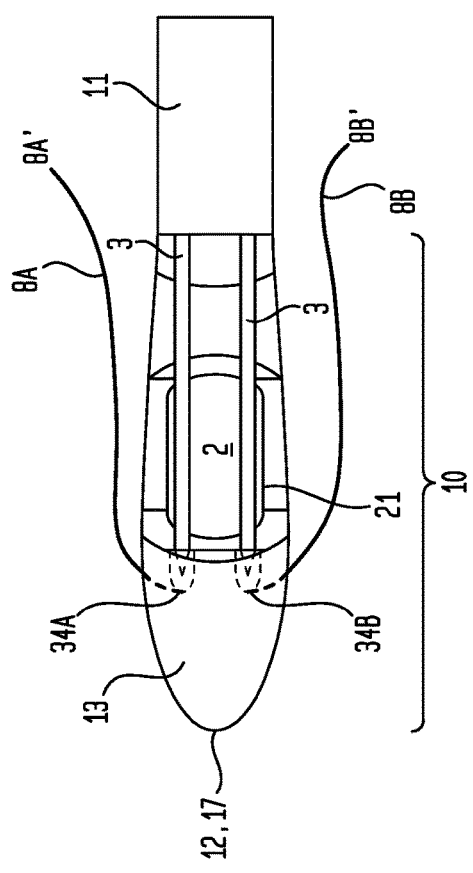
FIG. 17 is a top plan view of an embodiment of the suturing probe having a pair of thread carriers correspondingly extended into the pair of thread capture chambers to corresponding engage a pair of thread lappets retained in the pair of thread capture chambers.
Figure 16:
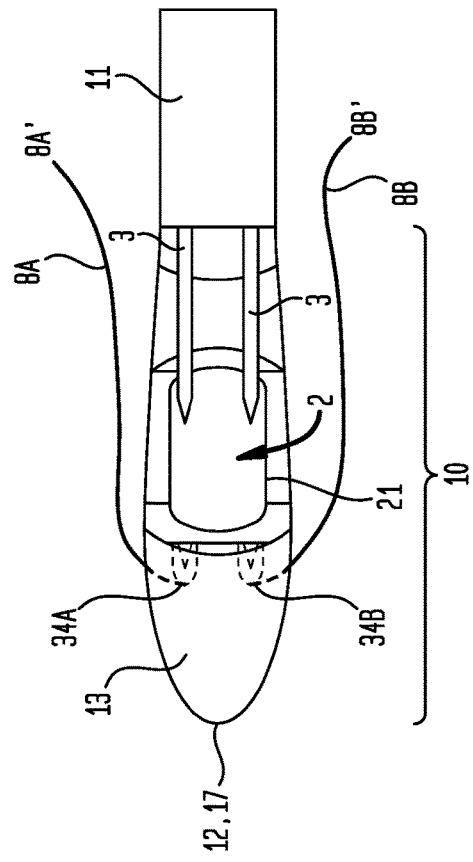
FIG. 16 is a top plan view of an embodiment of the suturing probe having a pair of thread carriers and a corresponding pair of thread capture chambers each retaining a thread lappet including a thread.
Figure 18:
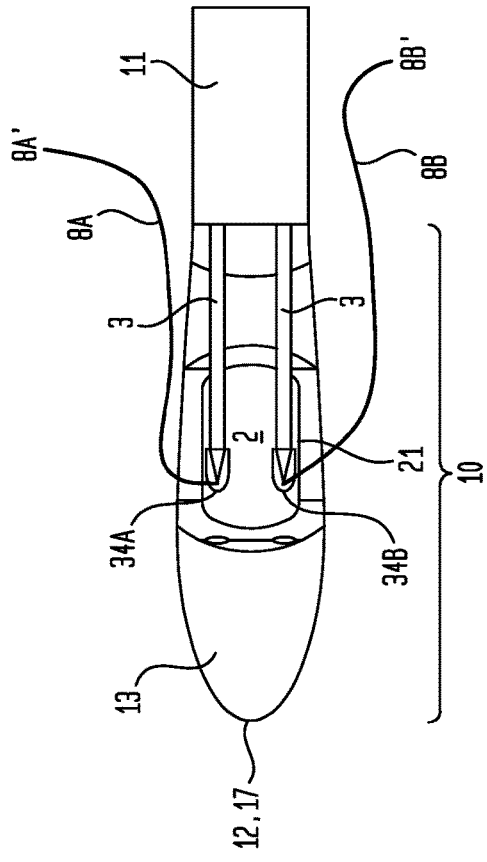
FIG. 18 is a top plan view of an embodiment of the suturing probe including a pair of thread carriers retracted from the corresponding pair of thread capture chambers to carry the pair thread lappets.

Now, with primary reference to FIGS. 12 and 13, in particular embodiments, the external surface of the recessed portion (24) of the suturing probe external surface (13) disposed about and in the thread capture chamber passage (32) through which the thread carrier (3) passes into the thread capture chamber (7) can be configured as a thread lappet receiver (33) which can receive and retain a thread lappet (34, 34A, 34B) having an outwardly extending thread (8). Each of the one or more thread carriers can be coupled to a drive member first end (42)(as shown in the example of FIG. 13) and extends axially outward to terminate in a thread carrier terminal end (6). The thread carrier (3) can comprise a slender rod which can, but need not necessarily, taper approaching the thread carrier terminal end (6). The taper can be sufficient to allow the thread carrier (6) to pass through a particular type of substrate (15), and in particular embodiments, pass into or through the lappet body (34) to enter the thread capture chamber (7), and as to particular embodiments, the thread carrier (3) can taper to a sharp point at the thread carrier terminal end (6) to pass through a substrate (15) comprising animal tissue.

Now, with primary reference to FIGS. 14 and 15, the thread lappet (34) can, but need not necessarily, comprise a closed end tubular lappet body (35A). The lappet body external surface (36) can be configured to matingly engage the thread lappet receiver (33) to retain the lappet body (35A) within the thread capture chamber passage (32) through which the thread carrier (3) passes into the thread capture chamber (7). The lappet body internal surface (37) can define a lappet body interior space (38) to receive the thread carrier (3). The tubular lappet body (35A) can include a thread carrier capture element (41). As one example, can terminate at a lappet body annular peripheral margin (39) proximate the lappet body open end (40). The lappet body annular peripheral margin (39) can be sufficiently resilient to allow the thread carrier terminal end (6) to pass into the tubular lappet body (35A). The resilient property of the lappet body annular peripheral margin (39) can comprise a resilient material which resiliently stretches to allow ingress of the thread carrier terminal end (6).

Again, with primary reference to FIGS. 14 and 15, in particular embodiments, the lappet body (34) may not include a tubular lappet body (35), but rather a solid lappet body (35B) with attached thread (8). The lappet body external surface (36) can be configured to matingly engage the thread lappet receiver (33) to fix the lappet body (35A) within or over the thread capture chamber passage (32) through which the thread carrier (3) passes into the thread capture chamber (7). The thread carrier (3) can pierce the lappet body (34) entering the thread capture chamber (7) and the lappet body (34) can slidingly engage the thread carrier (3). The solid lappet body (35B) can be sufficiently resilient to allow the thread carrier terminal end (6) to pass into or through the solid lappet body (35B). The resilient property of the solid lappet body (35B) can resiliently stretch to allow the thread carrier terminal end (6) to pass into or through the solid lappet body (35B) and sufficient resiliently contract about the thread carrier (3) to allow delivery to or removal from the lappet body receiver (33).

Again, with primary reference to FIG. 14 through 18, each of the one or more thread carriers (3) can further include a lappet body capture element (43) which passes into or through the lappet body (34) and upon withdrawing the thread carrier (3) from the thread capture chamber (7) retains the lappet body (34) proximate the thread carrier terminal end (6) and can be drawn through the substrate (15) disposed in the substrate capture chamber (2) to correspondingly pass the thread (8) through the substrate (15). In particular embodiments, the lappet body capture element (43) can comprise an annular groove (43A) or an annular ring (43B) or a portion there of disposed proximate the thread carrier terminal end (6) of the thread carrier (3). In particular embodiments, the lappet body annular peripheral margin (39) can slidingly engage the thread carrier (3) and radially contract to be received and retained in the annular groove (43A). In particular embodiments, the lappet body (34) pierced by the thread carrier (3) can slidingly engage the thread carrier (3) and radially contract to be received and retained in the annular groove (43A). In particular embodiments, the lappet body (34) pierced by the thread carrier (3) can slidingly engage the thread carrier (3) to pass over the annular ring (43B) and radially contract about the thread carrier (3) to abut the annular ring (43B) against the lappet body (34). Upon axially retracting the thread carrier (3) into tubular member (11), the lappet body (34) can engage the external surface of the recessed external surface (24) of the suturing probe (10) opposite the thread capture chamber (7) and the one or more thread carriers (3) can be slidably disengaged from the lappet body (34).

Figure 19:
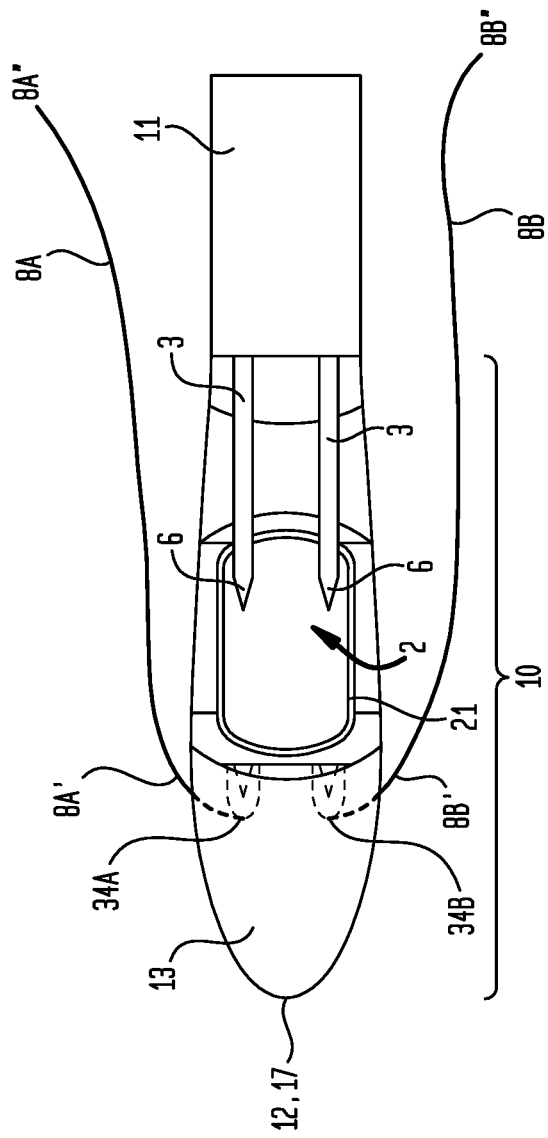
FIG. 19 is a top plan view of an embodiment of the suturing probe including a pair of extendable thread carriers and a thread capture chamber configured to retain a pair of thread lappets each having a thread extending from a lappet body.
Figure 20:
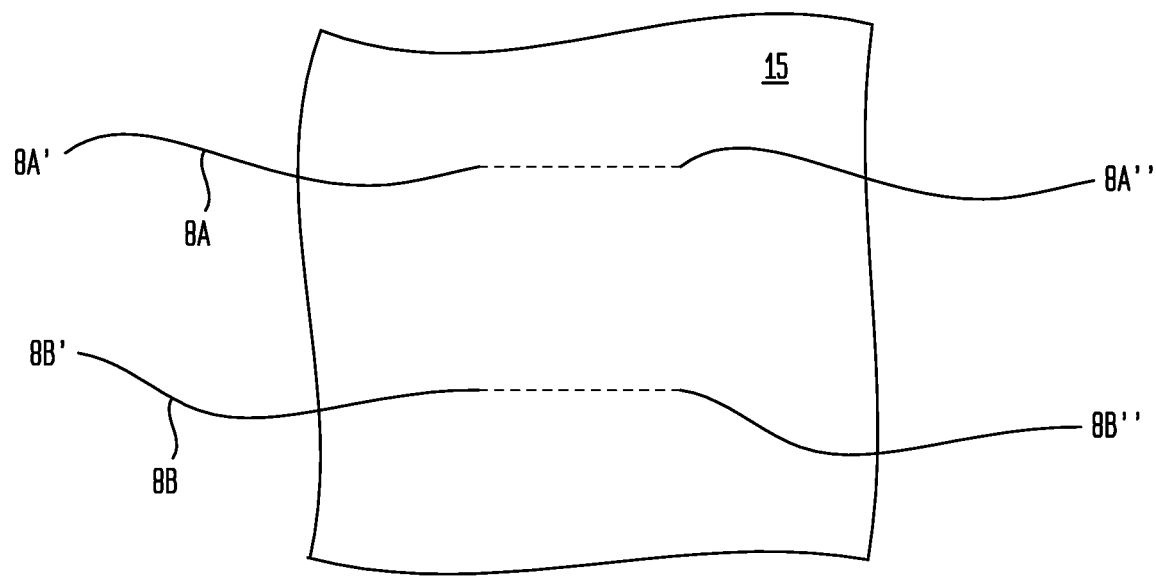
FIG. 20 is an illustration of a pair of threads disposed in a substrate by operation of the embodiment of the suturing probe shown in FIG. 19.

Now, with primary reference to FIGS. 19 and 20, in particular embodiments in which two lappet bodies (34A)(34B) each have an extending discrete thread (8A)(8B)(as shown in the example of FIG. 19), by operation of the suturing apparatus (1) the medial portion of each of the discrete threads (8A)(8B) can be disposed in spaced apart relation in the substrate (15) (as shown in the example of FIG. 20). Subsequently, each of the two pairs of thread ends (8A')(8A") and (8B')(8B") can be knotted in various combinations to dispose the pair of threads (8A)(8B) in the substrate (15) as a pair of discrete sutures (44A)(44B) disposed in spaced apart relation in the substrate (15) (as shown in the example of FIG. 29), or the first end of a first thread (8A') can be knotted with the second end of the second thread (8B") and the second end of the first thread (8A") can be knotted with the first end of the second thread (8B') to form one thread loop (44C) in which the thread crosses over the substrate (as shown in the example of FIG. 29), or the first ends of each thread can be knotted and the second ends of the thread can be knotted to form one thread loop (44D) having portions of the thread loop disposed in generally parallel relation on the substrate (15) (as shown in the example of FIG. 29).

Figure 21:
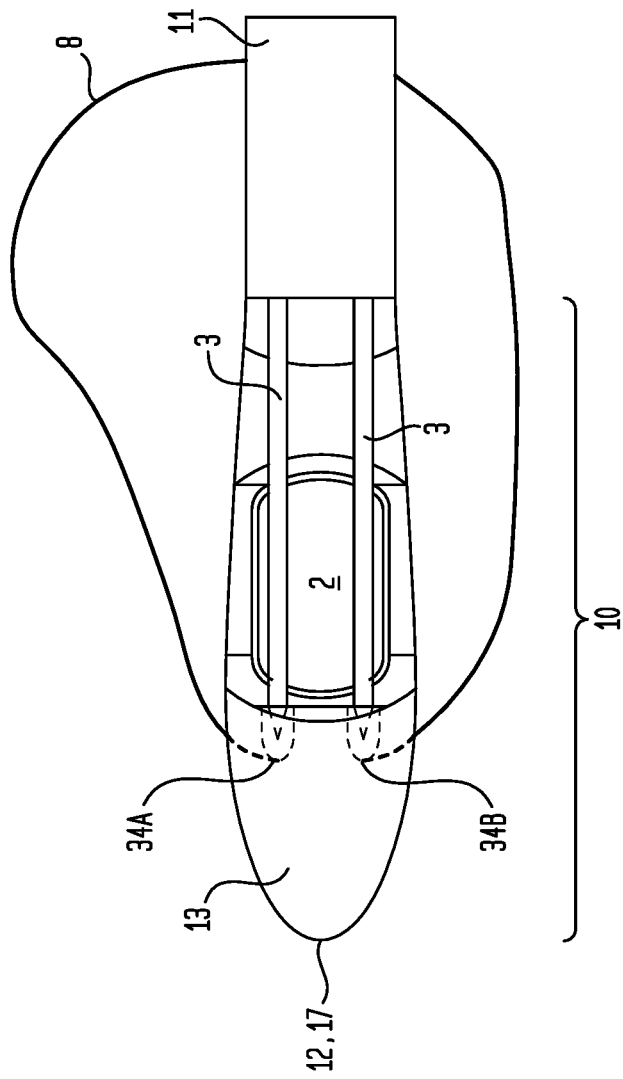
FIG. 21 is a top plan view of an embodiment of the suturing probe having a pair of extendable thread carriers and a thread capture chamber configured to retain a pair of thread lappets having one thread extending between a pair of lappet bodies.
Figure 22:
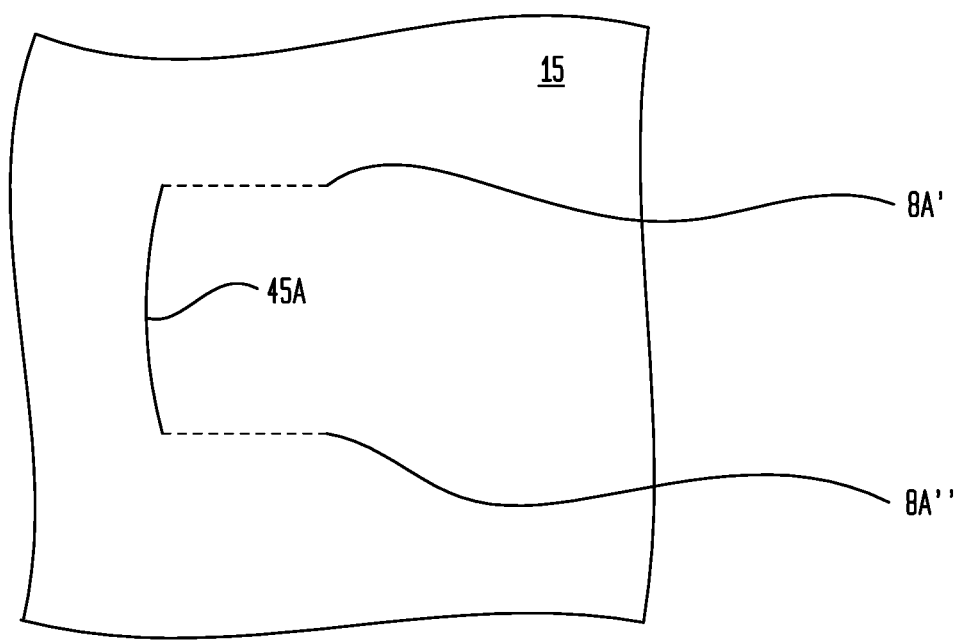
FIG. 22 is an illustration of a thread disposed in a substrate by operation of the embodiment of the suturing probe shown in FIG. 21.

Now, with primary reference to FIGS. 21 and 22, in embodiments in which one thread (8) has a common length disposed between two lappet bodies (34A)(34B) (as shown in the example of FIG. 21) then a pair of sutures (44A)(44B) can be disposed in spaced apart relation in the substrate (15) and the pair thread ends (8A')(8A") can be knotted forming thread portions (45A')(45A") disposed in generally parallel relation on the substrate (15) (as shown in the example of FIG. 31).

Figure 23:
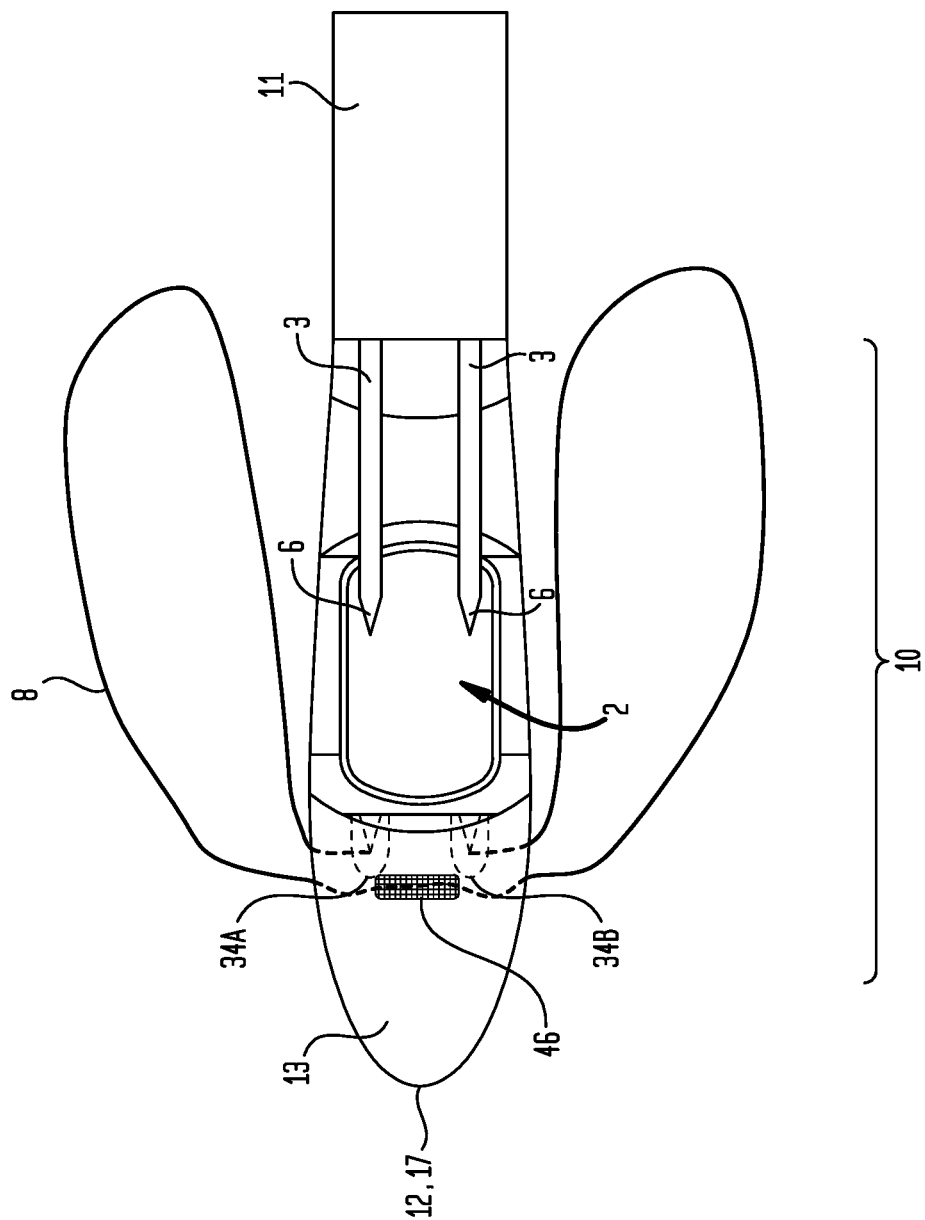
FIG. 23 is a top plan view of an embodiment of the suturing probe having a pair of extendable thread carriers and a thread capture chamber configured to retain a pair of thread lappets having a thread extending between a pair of lappet bodies and a pledget disposed medially on the thread.
Figure 24:
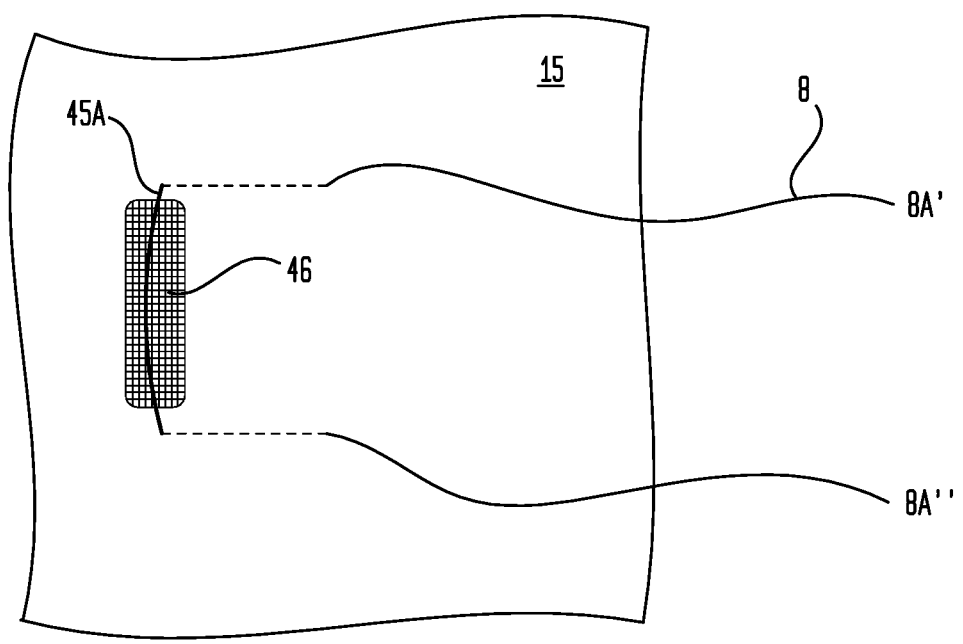
FIG. 24 is an illustration of a thread with pledget disposed in a substrate by operation of the embodiment of the suturing probe shown in FIG. 23.
Figure 34:
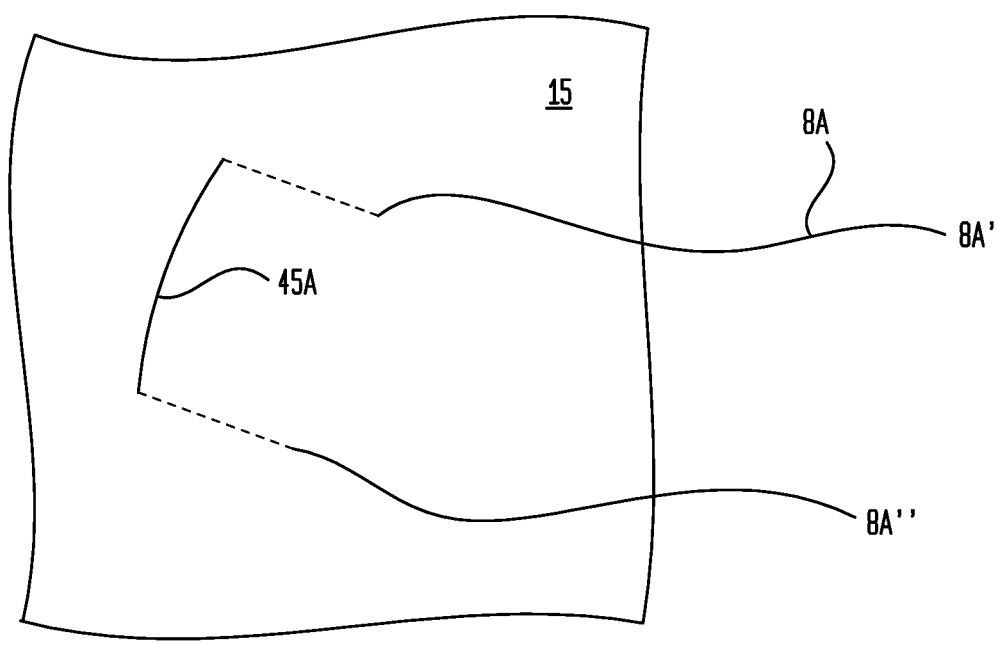
FIG. 34 is an illustration of a suture disposed in a substrate by capturing the substrate in a substrate capture chamber as shown FIG. 32B and drawing the pair of thread ends of one tread through the substrate by operation of embodiments of the suturing probe and joining the thread first and second ends.
Figure 35:
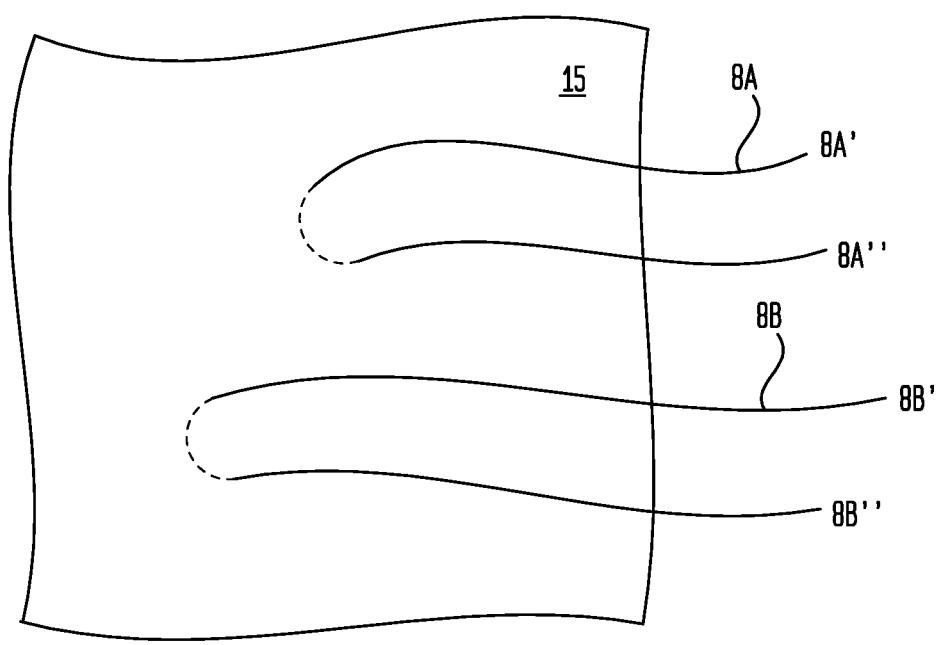
FIG. 35 is an illustration of the resultant position of a pair of sutures in the substrate using the embodiment of the substrate capture chamber having the substrate capture chamber side wall configured as shown in FIG. 33B.

Now, with primary reference to FIGS. 23 and 24, in particular embodiments in which one thread (8) has a common length disposed between a pair of lappet bodies (34A)(34B) a pledget (46) can be disposed medially on the thread (8) (as shown in the example of FIG. 23 and when the thread carriers (3) are drawn through the substrate (15) the pledget (46) can be disposed on the substrate (15) between the portions of the thread passing through the substrate (15)(as shown in the example of FIG. 24).

Now with primary reference to FIG. 25, in particular embodiments, the suturing probe (10) can outward axially extend from a tubular member (11) to terminate in a probe tip (12) having a pair of suturing probe recessed external surfaces (24A)(24B)(each as above described) disposed in generally outwardly opposite facing relation (in certain embodiments mirror image relation) with a corresponding pair of substrate capture chambers (2A)(2B) each having a chamber port (21A)(21B) open to a corresponding one of the pair of recessed external surfaces (24A)(24B), as above described, and in particular embodiments a common chamber sidewall (19) terminating in a pair of chamber ports (21A)(21B)). One or more thread carriers (3) can operate to correspondingly pass within one of the recessed interior space (28A)(28B) correspondingly defined by each of the pair of recessed external surface (24A)(24B) of the suturing probe external surface (13) outside of the substrate capture chambers (2).

Now, with primary reference to FIG. 26, in particular embodiments, a thread carrier (3) can axially move between a retracted condition (5) toward an extended condition (6) in each of the pair of recessed interior spaces (28A)(28B) with the corresponding thread carrier (3A)(3B) in each of the pair of recesses (24) passing outside of the corresponding one of the pair of substrate capture chambers (2) into a corresponding thread lappet receiver (34A)(34B) of the thread capture chamber (7).

Now, with primary reference to FIG. 27, each of the thread carriers (3A)(3B) can capture a thread lappet (34) mounted in corresponding thread lappet receiver (34A)(34B) in the thread capture chamber (7). Retraction of the pair of thread carriers (3A)(3B) can draw a thread (8) through the corresponding recessed portion (24) of the suturing probe (10) upon return of the thread carrier (3) toward the retracted condition (5). In certain embodiments, both thread carriers (3A)(3B) can be coupled to a drive member first end (42) and upon movement of the drive member first end (42) be concurrently extended and retracted. In other embodiments, each tread carrier (3) can be coupled to a pair of drive member first ends (42) which independently operate to drive each of the pair of thread carriers (3A)(3B) independent of the other thread carrier (3A or 3B).

In the illustrative example of FIGS. 25 through 27, a pair of thread lappets (34A)(34B), disposed on opposite thread ends (8A')(8A") of one thread (8) (as shown in the example of FIG. 25) or on the thread ends (8A')(8B') of a pair of threads (8A)(8B)(as shown in the example of FIG. 19), can be mounted in the thread lappet receivers (33A)(33B) of the thread capture chamber (7). As shown in FIG. 25 through FIG. 27, each of the pair of substrate capture chambers (2A)(2B) can correspondingly open to the pair of recessed portions (24A)(24B) and can correspondingly capture a pair of substrates (15A)(15B)(as shown in the example of FIG. 28). The pair of thread carriers (3A)(3B) can be extended in the corresponding pair of recessed interior spaces (28A)(28B), whether concurrently or serially, to correspondingly pass through the pair of substrates (15) and through or into the corresponding pair of lappet bodies (34A)(34B) mounted in the thread capture chamber (7). The pair of thread carriers (3A)(3B) retaining the corresponding pair of lappet bodies (34A)(34B) can be retracted to draw the pair of thread ends (8A')(8A") through the respective one of the pair of substrates (15) captured in the pair of substrate capture chambers (2). If the thread (8) comprises a one thread (8) having the opposite pair of ends (8A')(8A") drawn through the corresponding pair of substrates (15A)(15B), the pair of ends (8A')(8A") can be knotted to secure the pair of substrates (15) in relation to each other as shown in the example of FIG. 28.

Now, with general reference to FIGS. 29 through 31, the use of the various embodiments of the suturing device (1), can result in a corresponding variety of suture (44) configurations made in a captured substrate (15). Now, with reference to FIG. 29, a discrete suture (44) or a plurality of discrete sutures (44) can be made in a substrate (15) by joining the opposite pair of thread ends (8A')(8A") of each thread (8) passed through the substrate (15). Now, with primary reference to FIG. 30, a continuous suture (44) can be made in the captured substrate (15) by joining the first thread end (8A') of a first thread (8A) with the second thread end (8B") of a second thread (8B). Now, with primary reference to FIG. 31, a suture (44) can be made in a substrate by drawing the pair of thread ends (8A')(8A") through the substrate (15) and joining the thread first and second ends (8A')(8A").

Now, with primary reference to FIGS. 32A and 32B, in particular embodiments, the substrate capture chamber (2) can be fixedly or adjustably disposed in the recessed portion (24) of the probe tip (12). As shown in the Figures the medial longitudinal axis (47) of the substrate capture chamber (2) can be disposed in angled relation to the longitudinal axis of the probe tip (48). This affords the advantage of positioning the substrate (15) in different spatial relations to the path of the thread carrier (3) to allow the thread (8) to pass through the substrate (15) in a path that affords a desired purchase of the suture (44) in the substrate (15). Now with reference to FIG. 34, which illustrates the resultant position of the suture (44) in the substrate (15) using the embodiment of the angled substrate capture chamber (2) shown in FIG. 32B.

Now, with primary reference to FIGS. 33A and 33B, in particular embodiments, the substrate capture chamber side wall (19) can be configured to urge the captured substrate (15) into a desired spatial relation to the path of the thread carrier(s) (3). As illustrated by FIG. 33A, the substrate (15) can be urged to conform with the substrate capture chamber side wall (19) to change the path of the thread carrier (3) through the substrate (15) in a first direction, and as illustrated by FIG. 33B, the substrate (15) can be urged to conform with the substrate capture chamber sidewall (19) in a second direction, different than the first direction, to change the path of the thread carrier(s) (3) through the substrate (15). Now, with reference to FIG. 35, which illustrates the resultant position of a pair of sutures (44A) (44B) in the substrate using the embodiment of the substrate capture chamber (2) having the substrate capture chamber side wall (19) configured as shown in FIG. 33B.

Now, with primary reference to FIGS. 36A and 36B, in particular embodiments, one thread (8) a having one of a pair of thread lappets (34A)(34B) attached to opposite thread ends (8A')(8A"), can have the first of the pair of thread lappets (34A) coupled to the thread carrier terminal end (6) of a first of a pair of thread carriers (3), and the second of the pair of thread lappets (34b) can be mounted to the thread lappet receiver (33) of the thread capture chamber (7). Extension of the pair of thread carriers (3) drives the first of the pair of thread lappets (34A) mounted on the thread carrier terminal end (6) of the first thread carrier (3) through the captured substrate (15), while the second thread lappet (34B) mounted to the thread lappet receiver (33) engages the thread carrier terminal end (6) of the second thread carrier (3) and retraction of the pair of thread carriers (3) draws the second thread lappet (34B) through the substrate (15).

Now, with reference to FIG. 37A, the which illustrates the resultant path of the thread (8) in the substrate (15), and FIG. 37B illustrates the resultant suture (44) in the substrate (15) upon joining the pair of thread ends (8A')(8A").

Now, with primary reference to FIG. 38, particular embodiments of the suturing apparatus (1) can further include three or more thread carriers (3) which operate as above described to pass or draw a plurality of threads (8) through a substrate (15) captured in the substrate capture chamber (2) to dispose the plurality of threads (8) in the substrate (15) as above described and joining the tread ends (8A')(8A")(8B')(8B") in various combinations to obtain various forms of a suture (44) in the substrate (15).

As can be easily understood from the foregoing, the basic concepts of the present invention may be embodied in a variety of ways. The invention involves numerous and varied embodiments of a suturing apparatus and methods for making and using such suturing apparatus including the best mode.

As such, the particular embodiments or elements of the invention disclosed by the description or shown in the figures or tables accompanying this application are not intended to be limiting, but rather illustrative of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "suture" should be understood to encompass disclosure of the act of "suturing"—whether explicitly discussed or not—and, conversely, were there effectively disclosure of the act of "suturing", such a disclosure should be understood to encompass disclosure of a "suture" and even a "means for suturing." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in Merriam-Webster's Collegiate Dictionary, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the suturing apparatus herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:
1. An apparatus, comprising:
a plurality of thread lappets each having an attached thread;
a suturing probe including a thread capture chamber having a plurality of thread lappet receivers each configured to retain one of said plurality of thread lappets with said attached thread, said thread capture chamber opening into a recessed external surface delimiting an open area of said suturing probe;
a substrate capture chamber having a chamber side wall extending from a chamber bottom to a chamber port defining a transition edge delimiting a substrate capture chamber entry in said recessed external surface of said suturing probe;

a plurality of slender rods each slidably disposed in said suturing probe, said plurality of slender rods extendable through said open area into a corresponding one of plurality of thread lappet receivers of said thread capture chamber, said plurality of slender rods comprise a first slender rod and a second slender rod, said first slender rod carrying a first thread lappet having a first thread extending to an unattached thread end, said second slender rod carrying a second thread lappet having a second thread extending to an unattached thread end, said first and second slender rods configured to carry said first and second thread lappets through a substrate captured by said substrate capture chamber to dispose said first thread and said second thread in spaced apart relation in said substrate, wherein a first end of said first thread is configured to be knotted with a second end of said second thread and a second end of the first thread can be knotted with a first end of said second thread to form one thread loop having a crossed portion of said thread loop disposed on said substrate, wherein first ends of said first and second threads are configured to be knotted and the second ends of said first and second thread are configured to be knotted to form one thread loop having portions of the thread loop disposed in generally parallel spaced apart relation on said substrate.

2. An apparatus, comprising:

a first thread lappet and second thread lappet joined by one thread;

a suturing probe including a thread capture chamber having a first thread lappet receiver and a second thread lappet receiver correspondingly configured to retain said first thread lappet and said second thread lappet, said thread capture chamber opening into a recessed external surface delimiting an open area of said suturing probe;

a substrate capture chamber having a chamber side wall extending from a chamber bottom to a chamber port defining a transition edge delimiting a substrate capture chamber entry in said recessed external surface of said suturing probe;

a first slender rod and a second slender rod each slidably disposed in said suturing probe, said first slender rod and said second slender rod each extendable through said open area into said first lappet receiver and said second thread lappet receiver of said thread capture chamber, said first thread lappet disposed on said first slender rod, said second thread lappet disposed in said second thread lappet receiver of said second thread capture chamber, said first slender rod configured to drive said first thread lappet through said substrate captured by said substrate capture chamber and into said first lappet receiver, said second slender rod configured to draw said second thread lappet from said second lappet receiver through said substrate captured by said substrate capture chamber, wherein a medial portion of said one thread is configured to be disposed diagonally on said substrate between end portions of said thread, said end portions are configured to be knotted to form one thread loop having a crossed portion of said thread loop disposed on said substrate.

* * * * *